US012788965B2

(12) United States Patent
Afanasewicz et al.

(10) Patent No.: US 12,788,965 B2
(45) Date of Patent: Nov. 10, 2026

(54) VENTRICULAR ASSIST DEVICE CUFF LOCKS AND METHODS OF USE

(71) Applicant: TC1 LLC, St. Paul, MN (US)

(72) Inventors: Elizabeth Afanasewicz, Allston, MA (US); Grey Nagle, Wilmington, MA (US); Christopher Grace, St. Paul, MN (US)

(73) Assignee: TC1 LLC, St. Paul, MN (US)

( * ) Notice: Subject to any disclaimer, the term of this patent is extended or adjusted under 35 U.S.C. 154(b) by 89 days.

(21) Appl. No.: 18/991,239

(22) Filed: Dec. 20, 2024

(65) Prior Publication Data

US 2025/0213848 A1 Jul. 3, 2025

Related U.S. Application Data

(60) Provisional application No. 63/648,562, filed on May 16, 2024, provisional application No. 63/615,925, filed on Dec. 29, 2023.

(51) Int. Cl.
*A61M 60/863* (2021.01)
*A61M 60/165* (2021.01)

(52) U.S. Cl.
CPC ........ *A61M 60/863* (2021.01); *A61M 60/165* (2021.01); *A61M 2205/0216* (2013.01); *A61M 2205/583* (2013.01); *A61M 2210/125* (2013.01)

(58) Field of Classification Search
CPC .......................... A61M 60/863; A61M 60/165
See application file for complete search history.

(56) References Cited

U.S. PATENT DOCUMENTS 3,766,567 A 10/1973 Kahn et al.
4,099,759 A 7/1978 Kornhauser
(Continued)

FOREIGN PATENT DOCUMENTS

CA 2526920 C 2/2009
CN 1842354 A 10/2006
(Continued)

OTHER PUBLICATIONS

"Nickel Titanium", Wikipedia, Available online at: https://en.wikipedia.org/wiki/Nickel_titanium, Accessed from internet, Jul. 28, 2016, 9 pages.
(Continued)

*Primary Examiner* — Jonathan Ng
(74) *Attorney, Agent, or Firm* — Kilpatrick Townsend & Stockton LLP

(57) ABSTRACT

A ventricular assist device (VAD) includes an inlet cannula, a blood flow outlet, a blood pump assembly operable to pump blood from the inlet cannula to the blood flow outlet, and a coupling mechanism operable to secure the blood pump to a ventricular cuff attached to a heart. The coupling mechanism includes a coupling mechanism housing, a spring arm member attached to the coupling mechanism housing, and a cuff lock assembly including cuff lock arms slidably disposed within cuff lock passages defined by the coupling mechanism housing. The coupling mechanism is configured to accommodate repositioning of the cuff lock assembly from the retracted position to the engaged position when the blood pump is in the mounted configuration and block repositioning of the cuff lock assembly from the retracted position to the engaged position when the blood pump is not in the mounted configuration.

20 Claims, 40 Drawing Sheets

(56) References Cited

U.S. PATENT DOCUMENTS

| | | | | |
|---|---|---|---|---|
| 4,458,366 | A | 7/1984 | MacGregor | |
| 4,688,998 | A | 8/1987 | Olsen et al. | |
| 4,769,031 | A | 9/1988 | McGough et al. | |
| 5,055,005 | A | 10/1991 | Kletschka | |
| 5,098,369 | A | 3/1992 | Heilman et al. | |
| 5,139,517 | A | 8/1992 | Corral | |
| 5,195,877 | A | 3/1993 | Kletschka | |
| 5,222,980 | A | 6/1993 | Gealow | |
| 5,275,580 | A | 1/1994 | Yamazaki | |
| 5,456,714 | A | 10/1995 | Owen | |
| 5,470,208 | A | 11/1995 | Kletschka | |
| 5,708,346 | A | 1/1998 | Schob | |
| 5,814,005 | A | 9/1998 | Barra et al. | |
| 5,827,316 | A | 10/1998 | Young et al. | |
| 5,843,088 | A | 12/1998 | Barra et al. | |
| 5,984,956 | A | 11/1999 | Tweden et al. | |
| 6,001,056 | A | 12/1999 | Jassawalla et al. | |
| 6,050,975 | A | 4/2000 | Poirier | |
| 6,066,085 | A | 5/2000 | Heilman et al. | |
| 6,146,325 | A | 11/2000 | Lewis et al. | |
| 6,238,334 | B1 | 5/2001 | Easterbrook, III et al. | |
| 6,254,564 | B1 | 7/2001 | Wilk et al. | |
| 6,346,071 | B1 | 2/2002 | Mussivand | |
| 6,390,976 | B1 | 5/2002 | Spence et al. | |
| 6,669,708 | B1 | 12/2003 | Nissenbaum et al. | |
| 6,673,043 | B1 | 1/2004 | Landesberg | |
| 6,689,147 | B1 | 2/2004 | Koster, Jr. | |
| 6,705,988 | B2 | 3/2004 | Spence et al. | |
| 6,726,648 | B2 | 4/2004 | Kaplon et al. | |
| 6,732,501 | B2 | 5/2004 | Yu et al. | |
| 6,802,806 | B2 | 10/2004 | McCarthy et al. | |
| 6,808,498 | B2 | 10/2004 | Laroya et al. | |
| 6,863,677 | B2 | 3/2005 | Breznock | |
| 6,942,672 | B2 | 9/2005 | Heilman et al. | |
| 6,994,666 | B2 | 2/2006 | Shannon et al. | |
| 7,018,384 | B2 | 3/2006 | Skakoon | |
| 7,048,681 | B2 | 5/2006 | Tsubouchi et al. | |
| 7,056,286 | B2 | 6/2006 | Ravenscroft et al. | |
| 7,077,801 | B2 | 7/2006 | Haverich | |
| 7,214,234 | B2 | 5/2007 | Rapacki et al. | |
| 7,303,553 | B2 | 12/2007 | Ott | |
| 7,404,792 | B2 | 7/2008 | Spence et al. | |
| 7,462,019 | B1 | 12/2008 | Allarie et al. | |
| 7,824,358 | B2 | 11/2010 | Cotter et al. | |
| 8,152,845 | B2 | 4/2012 | Bourque | |
| 8,343,028 | B2 | 1/2013 | Gregoric et al. | |
| 8,500,759 | B2 | 8/2013 | Koyfman et al. | |
| 8,579,790 | B2 | 11/2013 | Jeffery et al. | |
| 9,144,637 | B2 | 9/2015 | Callaway et al. | |
| 9,199,019 | B2 | 12/2015 | Callaway et al. | |
| 9,750,858 | B2 | 9/2017 | Callaway et al. | |
| 9,981,076 | B2 | 5/2018 | Callaway et al. | |
| 10,111,993 | B2 | 10/2018 | Callaway et al. | |
| 10,525,177 | B2 | 1/2020 | Callaway et al. | |
| 11,185,683 | B2 | 11/2021 | Callaway et al. | |
| 11,583,671 | B2 | 2/2023 | Nguyen et al. | |
| 11,944,799 | B2 | 4/2024 | Bourque | |
| 2002/0045846 | A1 | 4/2002 | Kaplon et al. | |
| 2002/0095210 | A1 | 7/2002 | Finnegan et al. | |
| 2003/0023255 | A1 | 1/2003 | Miles et al. | |
| 2003/0040765 | A1 | 2/2003 | Breznock | |
| 2003/0130668 | A1 | 7/2003 | Nieman et al. | |
| 2004/0002624 | A1 | 1/2004 | Yu et al. | |
| 2004/0054251 | A1 | 3/2004 | Liotta | |
| 2004/0153112 | A1 | 8/2004 | Nissenbaum et al. | |
| 2004/0171905 | A1 | 9/2004 | Yu et al. | |
| 2004/0236170 | A1 | 11/2004 | Kim | |
| 2005/0033107 | A1* | 2/2005 | Tsubouchi .......... | A61M 60/859 600/6 |
| 2005/0101982 | A1 | 5/2005 | Ravenscroft et al. | |
| 2005/0131451 | A1 | 6/2005 | Kleshinski et al. | |
| 2005/0149093 | A1 | 7/2005 | Pokorney | |
| 2005/0154411 | A1 | 7/2005 | Breznock et al. | |
| 2005/0209502 | A1 | 9/2005 | Schmid et al. | |
| 2005/0251187 | A1 | 11/2005 | Beane et al. | |
| 2006/0036313 | A1 | 2/2006 | Vassiliades | |
| 2006/0064159 | A1 | 3/2006 | Porter et al. | |
| 2006/0089707 | A1 | 4/2006 | Vassiliades et al. | |
| 2006/0099716 | A1 | 5/2006 | Tipler et al. | |
| 2006/0142634 | A1 | 6/2006 | Anstadt et al. | |
| 2006/0161193 | A1 | 7/2006 | Beane et al. | |
| 2007/0088375 | A1 | 4/2007 | Beane et al. | |
| 2007/0100363 | A1 | 5/2007 | Dollar et al. | |
| 2007/0106315 | A1 | 5/2007 | Gregoric et al. | |
| 2007/0134993 | A1 | 6/2007 | Tamez et al. | |
| 2007/0167968 | A1 | 7/2007 | Pandey | |
| 2007/0167969 | A1 | 7/2007 | Pandey | |
| 2007/0173879 | A1 | 7/2007 | Pandey | |
| 2007/0265643 | A1 | 11/2007 | Beane et al. | |
| 2008/0009668 | A1 | 1/2008 | Cohn | |
| 2008/0009887 | A1 | 1/2008 | Cohn | |
| 2008/0009891 | A1 | 1/2008 | Cohn | |
| 2008/0076959 | A1 | 3/2008 | Farnan et al. | |
| 2009/0012552 | A1 | 1/2009 | Pandey et al. | |
| 2009/0143638 | A1 | 6/2009 | Keogh et al. | |
| 2009/0171136 | A1 | 7/2009 | Shambaugh, Jr. | |
| 2010/0305692 | A1 | 12/2010 | Thomas et al. | |
| 2011/0118766 | A1* | 5/2011 | Reichenbach ...... | A61M 60/237 606/153 |
| 2011/0118829 | A1 | 5/2011 | Hoarau et al. | |
| 2011/0118833 | A1 | 5/2011 | Reichenbach et al. | |
| 2011/0160850 | A1* | 6/2011 | Bourque ............. | A61M 60/178 623/3.1 |
| 2011/0245582 | A1 | 10/2011 | Zafirelis et al. | |
| 2012/0010455 | A1 | 1/2012 | Reichenbach et al. | |
| 2012/0035411 | A1 | 2/2012 | LaRose et al. | |
| 2012/0046514 | A1 | 2/2012 | Bourque | |
| 2012/0059212 | A1 | 3/2012 | LaRose et al. | |
| 2012/0165931 | A1 | 6/2012 | Bourque | |
| 2012/0226096 | A1 | 9/2012 | Callaway et al. | |
| 2014/0067057 | A1* | 3/2014 | Callaway ............ | A61M 60/232 623/3.26 |
| 2015/0273124 | A1* | 10/2015 | Callaway ............ | A61M 60/857 623/3.26 |
| 2015/0335802 | A1 | 11/2015 | Callaway et al. | |
| 2015/0359952 | A1 | 12/2015 | Andrus et al. | |
| 2016/0051738 | A1* | 2/2016 | Callaway ............ | A61M 60/861 623/3.26 |
| 2017/0266358 | A1* | 9/2017 | Aber .................. | A61M 60/148 |
| 2018/0333524 | A1* | 11/2018 | Callaway ............ | A61M 60/863 |
| 2021/0085845 | A1* | 3/2021 | West .................. | A61M 60/148 |
| 2021/0121677 | A1* | 4/2021 | Nguyen .............. | A61M 60/863 |
| 2022/0249831 | A1* | 8/2022 | Mitchell .............. | A61M 60/117 |
| 2022/0296876 | A1* | 9/2022 | Callaway ............ | A61M 60/232 |

FOREIGN PATENT DOCUMENTS

| | | | |
|---|---|---|---|
| DE | 10108809 | A1 | 9/2002 |
| EP | 1706168 | A1 | 10/2006 |
| EP | 2822614 | A1 | 1/2015 |
| EP | 2890418 | A1 | 7/2015 |
| EP | 2995327 | | 3/2016 |
| JP | 2003501154 | A | 1/2003 |
| JP | 2007510522 | A | 4/2007 |
| JP | 2009518141 | A | 5/2009 |
| JP | 2013510691 | A | 3/2013 |
| JP | 2015512687 | A | 4/2015 |
| WO | 0074747 | A1 | 12/2000 |
| WO | 03001980 | A2 | 1/2003 |
| WO | 2004014456 | A2 | 2/2004 |
| WO | 2004082742 | A1 | 9/2004 |
| WO | 2005046783 | A1 | 5/2005 |
| WO | 2005051838 | A2 | 6/2005 |
| WO | 2007038109 | A2 | 4/2007 |
| WO | 2008131453 | A1 | 10/2008 |
| WO | 2009085243 | A1 | 7/2009 |
| WO | 2011060386 | A2 | 5/2011 |
| WO | 2011081629 | A1 | 7/2011 |
| WO | 2012119073 | A1 | 9/2012 |
| WO | 2013134319 | A1 | 9/2013 |
| WO | 2014036060 | A1 | 3/2014 |
| WO | 20141 49892 | A1 | 9/2014 |

(56) References Cited

FOREIGN PATENT DOCUMENTS

| | | | | | |
|---|---|---|---|---|---|
| WO | 2015134944 | A1 | | 9/2015 | |
| WO | WO-2017218817 | A1 | * | 12/2017 | .......... A61M 60/216 |
| WO | 2023288097 | A1 | | 1/2023 | |

OTHER PUBLICATIONS

Barletta et al., "Design of a Bearing Less Blood Pump", Proc. Third International Symposium on Magnetic Suspension Technology, Jul. 1, 1996, pp. 265-274.

Thompson, "An Overview of Nickel-Titanium Alloys Used in Dentistry", International Endodontic Journal, vol. 33, Jul. 2000, pp. 297-310.

* cited by examiner

FIG. 9E
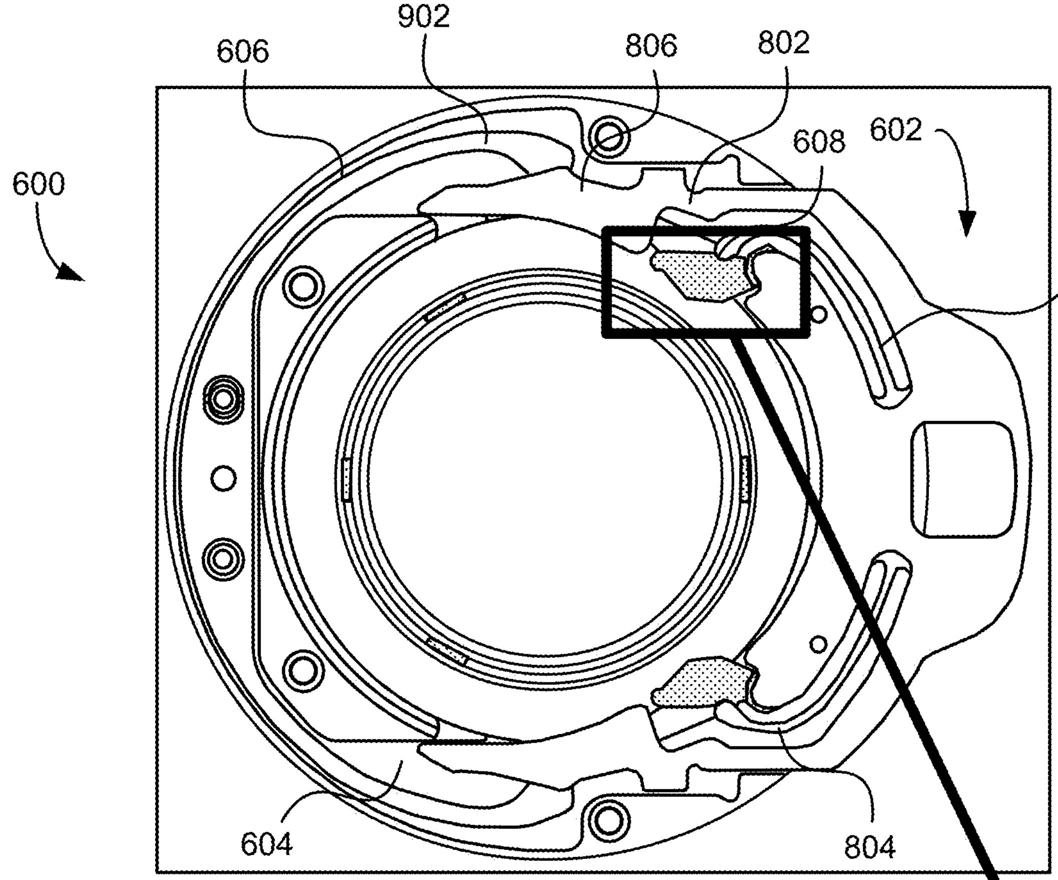
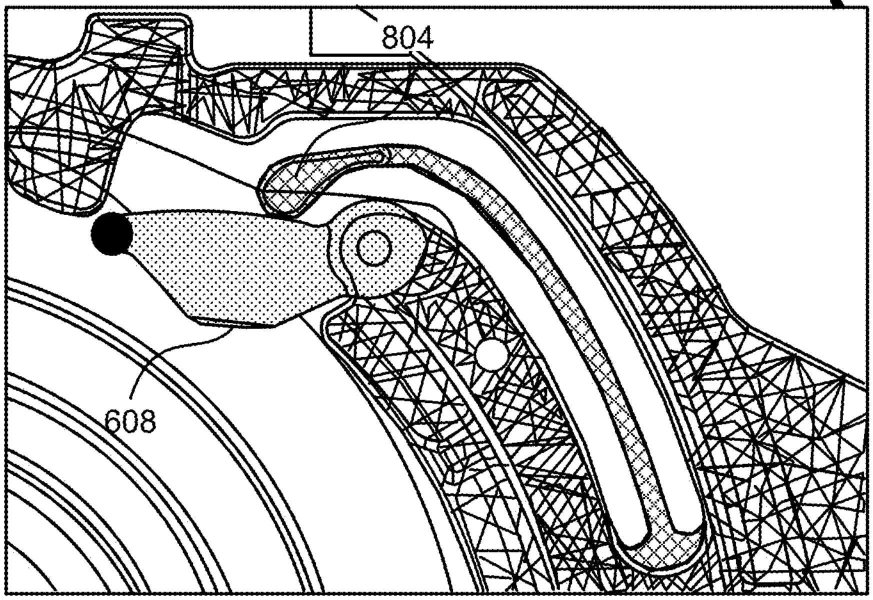
FIG. 9F 802
1402
1502
306
1406
710
1204

VENTRICULAR ASSIST DEVICE CUFF LOCKS AND METHODS OF USE

CROSS REFERENCE TO RELATED APPLICATION DATA

The present application claims the benefit of priority of U.S. Provisional Application No. 63/615,925 filed Dec. 29, 2023 and U.S. Provisional Application No. 63/648,562 filed May 16, 2024, the disclosures which are incorporated herein by reference in their entirety for all purposes.

TECHNICAL FIELD

This disclosure relates to ventricular assist device cuff locks.

BACKGROUND

Heart assist devices or pumps can be inserted in the circulatory system to pump blood from either a ventricle or atrium of a heart to the vasculature. A blood pump supplementing a ventricle is known as a ventricular assist device, or VAD. A VAD is useful when the ventricle alone is incapable of providing adequate blood flow.

BRIEF SUMMARY OF THE INVENTION

A continuing effort is being made to reduce the overall size and increase the efficiency of implantable medical devices. Ventricular assist devices (VAD) are particularly targeted for reduced size as the device is attached to a heart of a patient and semi-permanently implanted for pumping blood throughout the body. Accordingly, many advances have been made to reduce the size of the actual pump itself. The present invention provides devices and methods directed to improvements in corresponding coupling components for securing smaller blood pumps to attachment features (e.g., apical or ventricular cuffs) sewn into the heart of the patient.

Cuff locks may be used to secure a VAD to an apical cuff which is sewn directly onto the heart tissue. For example, the apical cuff may include a flange that is seated relative to the pump of the VAD. The flange is securely captured by a cuff lock to secure the VAD to the heart. A surgeon may secure the cuff lock in place by retracting a cuff lock from the pump, inserting the pump into the chest cavity, seating the pump onto the apical cuff, and pushing the cuff lock into a locked position. If the pump is not seated correctly onto the apical cuff, the cuff lock moves into what is called a "lockout" position. In a lockout position, the cuff lock is prone to damage as the surgeon forcefully pushes the cuff lock radially in toward the center of the pump, expecting the cuff lock to lock in place. The cuff lock assembly of the present disclosure advantageously enables a surgeon to quickly identify the lockout state and reposition the cuff lock assembly without damaging any components of the VAD system.

Various features of the present disclosure provide a VAD system that accommodates a smaller VAD footprint while preserving the cuff lock workflow and lockout capabilities. The present invention enhances the durability of the cuff lock during lockout and repositioning to reduce the occurrence of pump replacements during implantation procedures. For example, the radial travel length of cuff locks often makes them prone to bending moments when in the retracted position. If the cuff lock is damaged beyond proper function, either by forcing it inwards during lockout or by bending the cuff lock while retracted, the VAD must be replaced. The devices and methods of the present disclosure address these concerns and improve the durability of cuff locks and the reliability of secure attachment of the VAD to the apical cuff.

A ventricular assist device (VAD) according to the present disclosure includes an inlet cannula, a blood flow outlet, a blood pump assembly operable to pump blood from the inlet cannula to the blood flow outlet, and a coupling mechanism operable to secure the blood pump to a ventricular cuff attached to a heart. The ventricular cuff defines an inlet cannula passage for the inlet cannula and an outward facing circumferential flange having a groove. The coupling mechanism includes a coupling mechanism housing, a spring arm member attached to the coupling mechanism housing, and a cuff lock assembly including cuff lock arms slidably disposed within cuff lock passages defined by the coupling mechanism housing. The cuff lock assembly is repositionable relative to the coupling mechanism between an unlocked or retracted position and a locked or engaged position. The cuff lock assembly in the unlocked or retracted position accommodates insertion of the inlet cannula into the inlet cannula passage to mount the blood pump onto the ventricular cuff into a mounted configuration. The cuff lock arms extend over the outward facing circumferential flange of the ventricular cuff in the mounted configuration when the cuff lock assembly is in the locked or engaged position to secure the blood pump to the ventricular cuff. The spring arm member includes flexible arms configured to engage the cuff lock arms in the locked or engaged position to inhibit repositioning of the cuff lock arms relative to the coupling mechanism. The coupling mechanism is configured to accommodate repositioning of the cuff lock assembly from the unlocked or retracted position to the locked or engaged position when the blood pump is in the mounted configuration and block repositioning of the cuff lock assembly from the unlocked or retracted position to the locked or engaged position when the blood pump is not in the mounted configuration.

The ventricular assist device (VAD) may include various optional features. When the VAD is properly seated relative to the ventricular cuff, the cuff lock assembly may be positionable in a locked position, and, when the VAD is not properly seated relative to the ventricular cuff, the cuff lock assembly may be prevented from reaching the locked position. The coupling mechanism may further include two pivoting components that enable the cuff lock assembly to be positioned in the locked position or prevent the cuff lock assembly from reaching the locked position. When the VAD is properly seated relative into the ventricular cuff, the ventricular cuff flange may direct the two pivoting components to a first position that enables the cuff lock assembly to reach the locked position. When the VAD is not properly seated in the ventricular cuff, the two pivoting components are in a second position that prevents the cuff lock assembly from reaching the locked position. The cuff lock passages may define detents for protrusions of each of the two pivoting components to travel along. Each flexible arm of the spring arm member may engage with corresponding ridges on the cuff lock arms when the cuff lock assembly is in the locked position. The inlet cannula may have a longitudinal axis and the cuff lock assembly moves, relative to the cuff, from the unlocked position to the locked position transverse to the longitudinal axis. When the cuff lock assembly moves, relative to the cuff, from the unlocked position to the locked position in a plane perpendicular to the longitudinal axis. The cuff lock assembly may include a visual indicator where the visual indicator is exposed when the cuff lock assembly is not in the locked position and the visual indicator is obscured when the cuff lock assembly is in the locked position. The ventricular assist device may further include one or more stop components for engaging the cuff lock assembly and impeding the cuff lock assembly from reaching the locked position or enabling the cuff lock assembly to reach the locked position. When the VAD is properly seated against the flange of the cuff, the flange may compress the one or more stop components to a first position that enables the cuff lock to reach the locked position. When the VAD is not properly seated against the flange of the cuff, the one or more stop components may be raised to a second position by a spring, the second position preventing the cuff lock from reaching the locked position. The cuff lock passages may define detents for protrusions of each the one or more stop components to settle in in the first position. The one or more stop components may include a two-part cam component mechanism.

A method according to the present disclosure includes attaching a ventricular cuff to a heart and securing a ventricular assist device (VAD) to the ventricular cuff attached to the heart. The ventricular cuff includes an outward facing circumferential flange having a groove. The method further includes forming an opening in the myocardium and positioning an inlet cannula of a ventricular assist device (VAD) through a central opening of the ventricular cuff and into the opening in the myocardium. The method further includes securing the ventricular cuff to the VAD using a coupling mechanism. The coupling mechanism includes a coupling mechanism housing, a spring arm member attached to the coupling mechanism housing, and a cuff lock assembly comprising cuff lock arms slidably disposed within cuff lock passages defined by the coupling mechanism housing. The cuff lock assembly is repositionable relative to the coupling mechanism housing between a retracted position and an engaged position. The cuff lock assembly in the retracted position accommodates insertion of the inlet cannula into the inlet cannula passage to mount the VAD onto the ventricular cuff into a mounted configuration. The cuff lock arms are configured to extend over the outward facing circumferential flange of the ventricular cuff in the mounted configuration when the cuff lock assembly is in the engaged position to secure the VAD to the ventricular cuff. The spring arm member comprises flexible arms configured to engage the cuff lock arms in the engaged position to inhibit repositioning of the cuff lock arms relative to the coupling mechanism housing. The coupling mechanism is configured to accommodate repositioning of the cuff lock assembly from the retracted position to the engaged position in the mounted configuration and block repositioning of the cuff lock assembly from the retracted position to the engaged position when the VAD is not in the mounted configuration.

The method may include various optional steps. Each flexible arm of the spring arm member may engage with corresponding ridges on cuff lock arms when the cuff lock assembly is in the locked position. The coupling mechanism may further include two pivoting components to enable the cuff lock assembly to be positioned in the locked position or prevent the cuff lock assembly from reaching the locked position. The cuff lock assembly may include a visual indicator where the visual indicator is exposed when the cuff lock assembly is not in the locked position and the visual indicator is obscured when the cuff lock assembly is in the locked position. The inlet cannula may include a longitudinal axis and the cuff lock assembly moves, relative to the cuff, from the unlocked position to the locked position transverse to the longitudinal axis.

BRIEF DESCRIPTION OF THE DRAWINGS

A further understanding of the nature and advantages of the present disclosure may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 9E is a top view of a cuff lock system in a lockout configuration, in accordance with embodiments of the present disclosure.

FIG. 9F is an inset of the cuff lock system of FIG. 9D, in accordance with embodiments of the present disclosure.

DETAILED DESCRIPTION OF THE INVENTION

Figure 1:
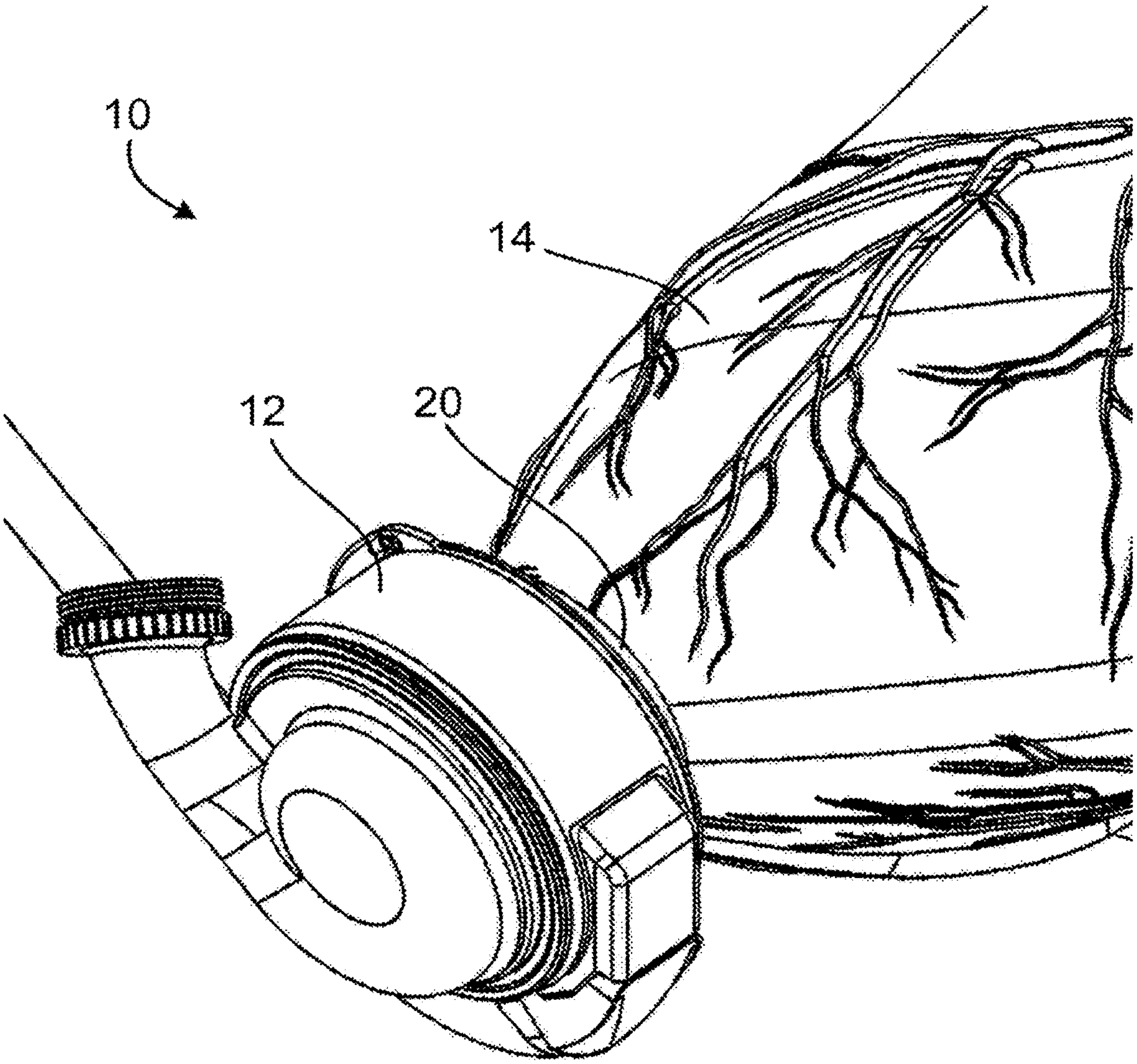
FIG. 1 is a perspective view of a blood pump installed at a heart, in accordance with embodiments of the present disclosure.

FIG. 1 is a perspective view of a blood pump installed at a heart. FIG. 1 includes a ventricular assist system 10 for treating, for example, a patient with a weakened left ventricle, includes a pump 12 that receives blood from a patient's heart 14. The pump 12 is coupled to a cuff 20, which in turn is attached to the heart 14. The cuff 20 is attached to the heart by, for example, sutures that attach a portion of the cuff 20 to the apex of the left ventricle of the heart 14. The pump 12 receives blood from the heart through an inflow cannula (not shown) of the pump 12 disposed through an opening in the cuff 20.

Figure 2:
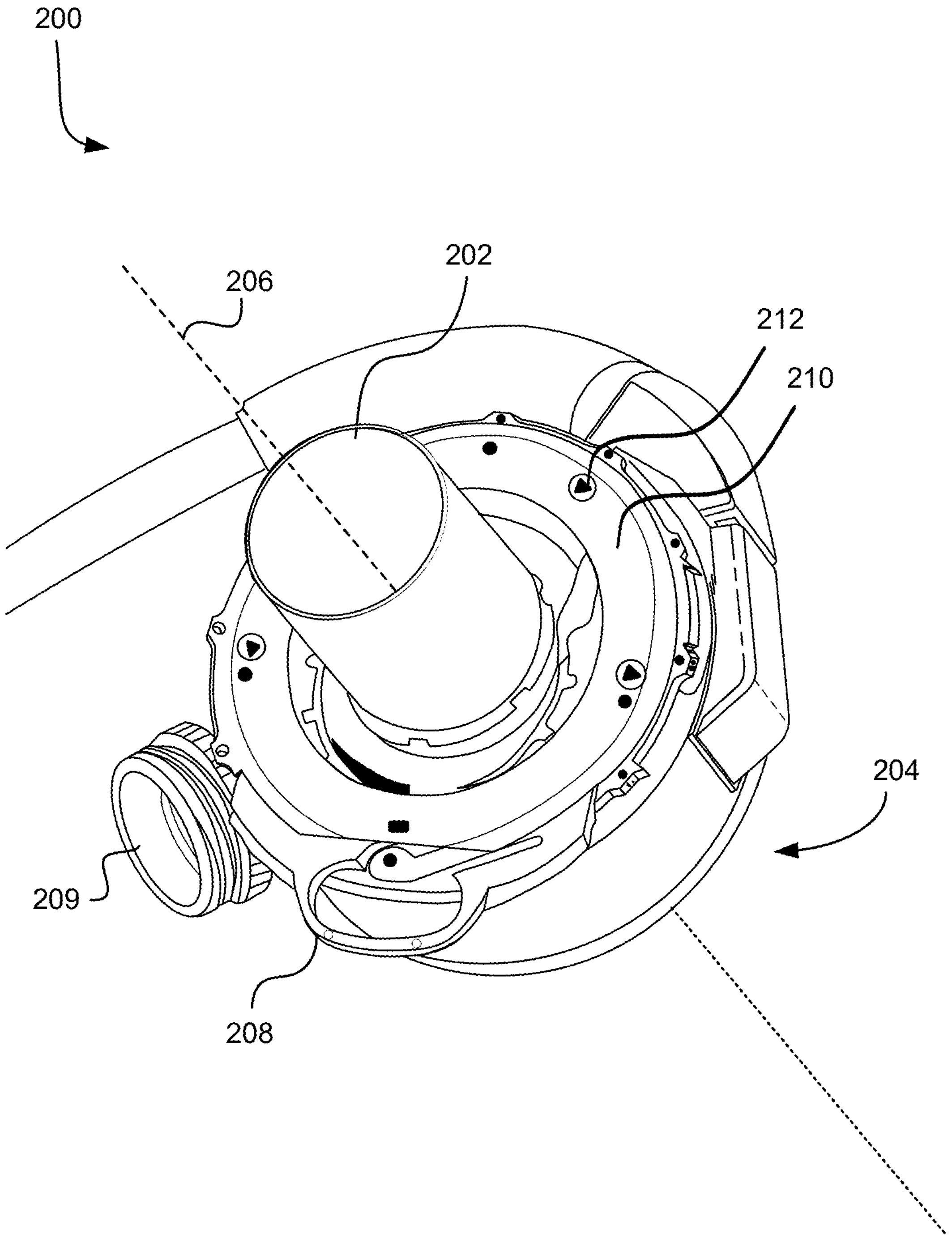
FIG. 2 is a perspective view of a blood pump and a cannula, in accordance with embodiments of the present disclosure.

FIG. 2 is a perspective view of a blood pump and a cannula. FIG. 2 illustrates another view of a ventricular assist system 200. In this view, an apical cuff is removed for clarity. System 200 includes an inlet cannula 202. As one having ordinary skill in the art would appreciate upon reading the present disclosure, an apical cuff includes an inlet cannula passage for the inlet cannula to extend through in an assembled system. The blood pump 204 receives blood from the heart through the inlet cannula 202 and the inlet cannula 202 defines a longitudinal axis 206. The blood pump 204 is operable to pump blood from the inlet cannula 202 to the blood flow outlet 209. A cuff lock assembly 208 moves, relative to the apical cuff (not shown) and the inlet cannula 202 from an unlocked position to a locked position transverse to the longitudinal axis 206, to be described in detail below. A cuff lock cover 210 is provided to cover and secure the cuff lock assembly 208 in the locked position. The cuff lock cover 210 may be secured to the blood pump 204 using screws 212, via welding, or the like.

Figure 3:
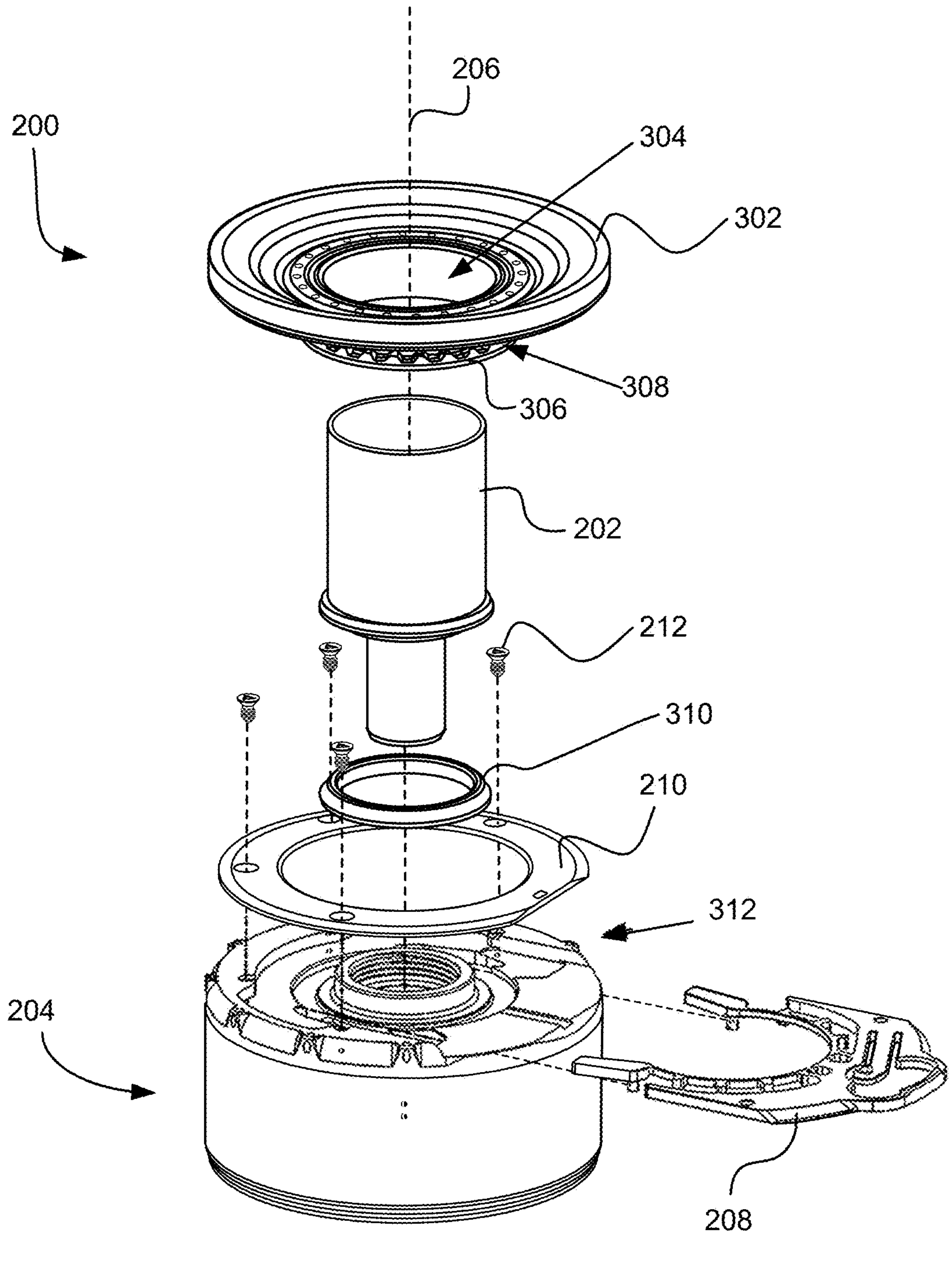
FIG. 3 is an exploded view of a cuff, a cannula, a cuff lock, and a blood pump, in accordance with embodiments of the present disclosure.

FIG. 3 is an exploded view of a cuff, a cannula, a cuff lock, and a blood pump. The description of system 10 and system 200 as described with respect to FIGS. 1-2 is relevant to the description of the exploded view described with respect to FIG. 3. Accordingly, similar components have similar numbering, form, and function unless otherwise noted herein. Visible in this exploded view, the system 200 further includes a ventricular cuff 302. A ventricular cuff may be interchangeably referred to as an apical cuff unless otherwise noted herein. The ventricular cuff 302 may be sewn or otherwise secured to the tissue of the heart as described above. The ventricular cuff 302 includes an inlet cannula passage 304 for the inlet cannula 202 and an outward facing circumferential flange 306 having a groove 308. In some embodiments, the groove 308 is a series of silicone "nubs" or "series of grooves" that are overmolded onto the circumferential flange 306 to prevent free rotation of the pump about the apical cuff, but allow the surgeon to apply a minimum amount of torque to intentionally rotate it about the cuff, if they need to make adjustments. One or more sealing elements 310 may be used at the interface of the inlet cannula 202 and the coupling mechanism 312 for sealing the blood pump 204.

According to various embodiments, a top surface of the blood pump 204 includes a coupling mechanism 312 that is operable to secure the blood pump 204 to the ventricular cuff 302 attached to the heart. The coupling mechanism 312 may be covered and housed in a coupling mechanism housing (e.g., the cuff lock cover 210). The coupling mechanism 312 may include one or more channels, pivoting components, stop components, etc., to be described in further detail below, that enable the cuff lock assembly 208 to advance to a locked position or that prevent the cuff lock assembly 208 from advancing to the locked position when the blood pump 204 is not properly seated relative to the ventricular cuff 302. In particular, the coupling mechanism 312 is configured to accommodate repositioning of the cuff lock assembly 208 from the retracted position to the engaged position when the blood pump 204 is in a mounted configuration (e.g., a properly seated configuration) and block repositioning of the cuff lock assembly 208 from the retracted position to the engaged position when the blood pump 204 is not in the mounted configuration.

Figure 4A:
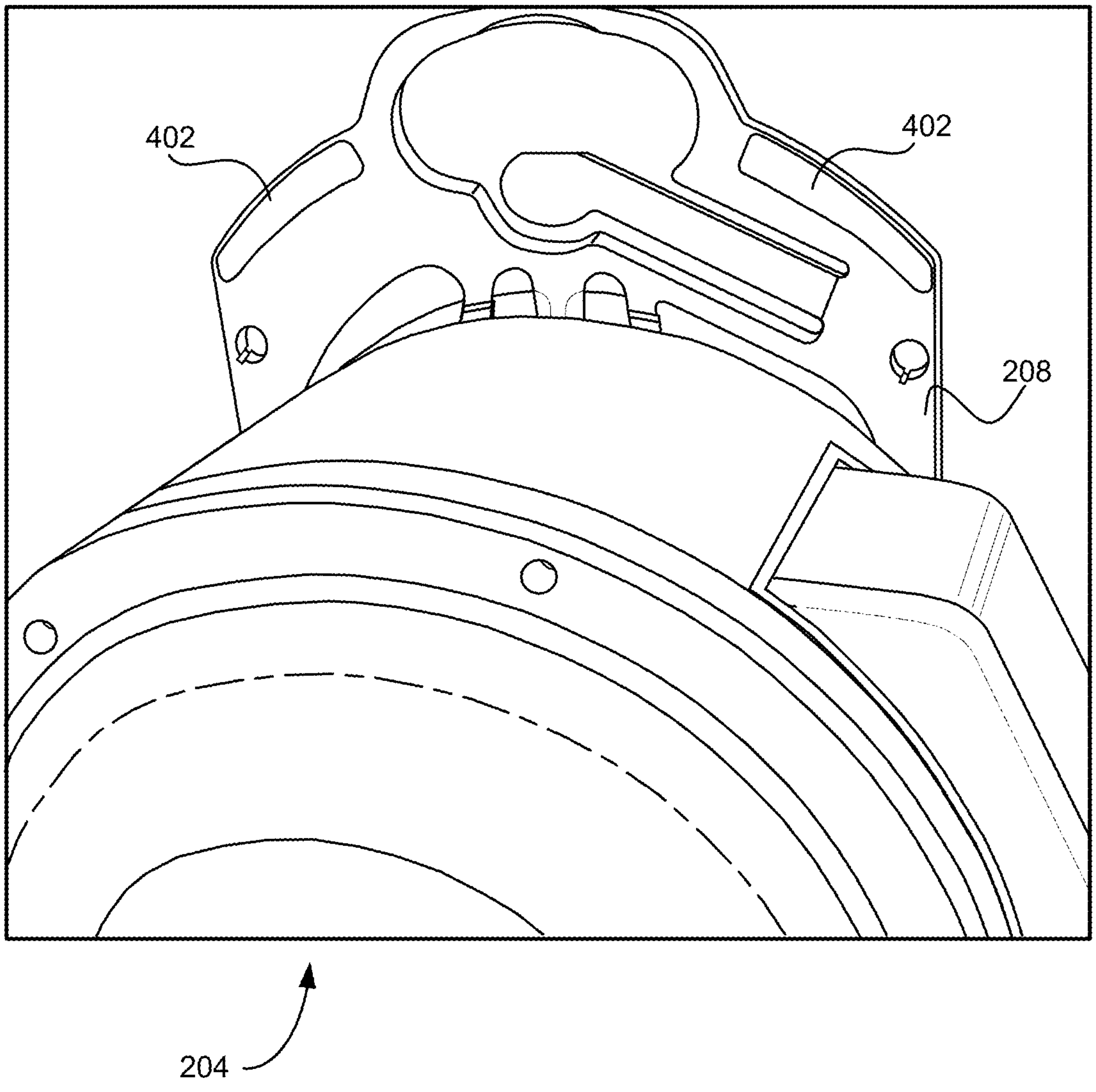
FIGS. 4A-4C illustrate a blood pump system in an unlocked configuration, in accordance with embodiments of the present disclosure.
Figure 4B:
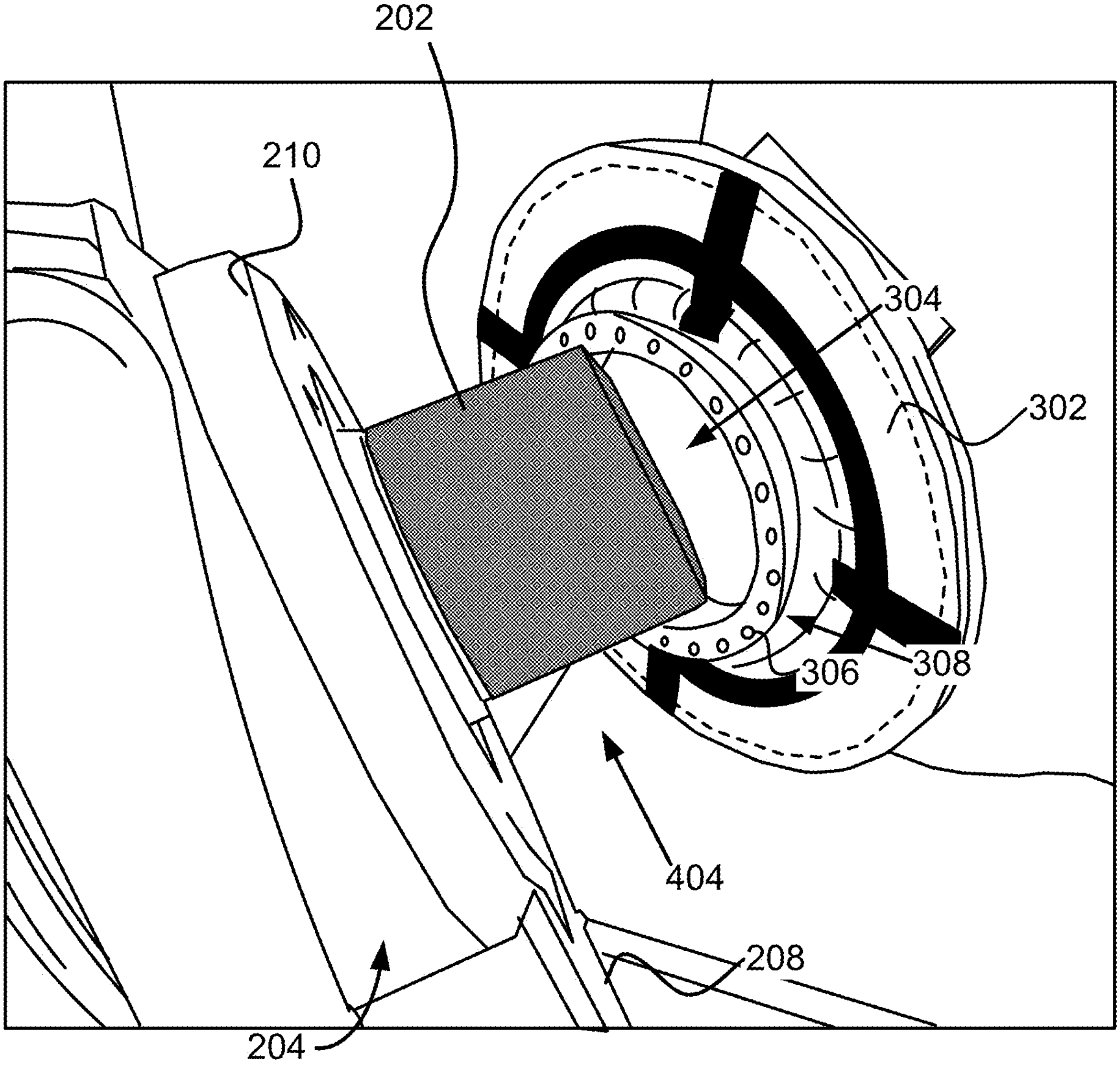
Figure 4C:
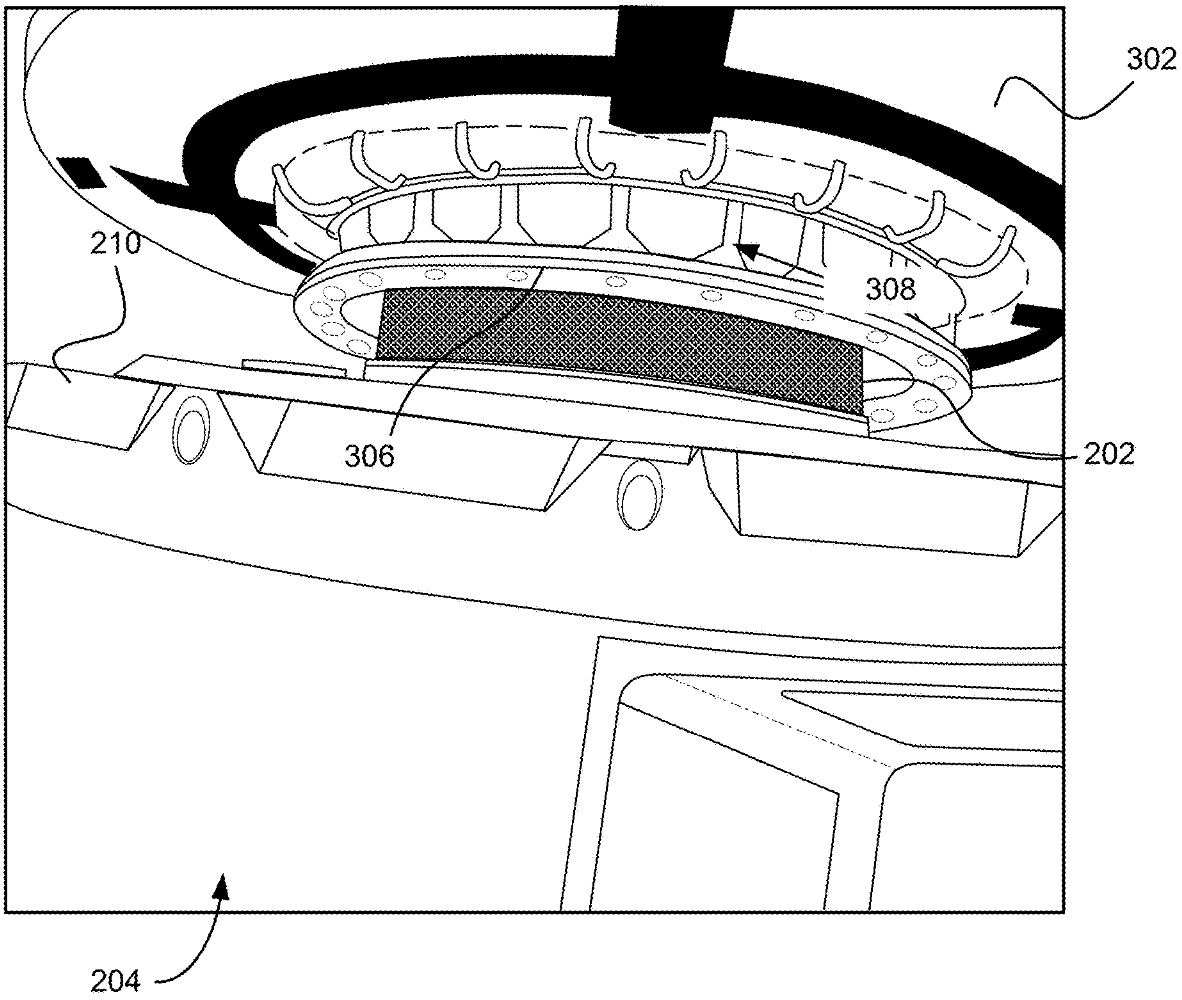

FIGS. 4A-4C illustrate a blood pump system in an unlocked configuration. The description of system 10 and system 200 as described with respect to FIGS. 1-3 is relevant to the description of the exploded view described with respect to FIGS. 4A-4C. Accordingly, similar components have similar numbering, form, and function unless otherwise noted herein. According to various embodiments, a cuff lock assembly includes one or more visual indicators 402 that are visible when the connection is not complete, e.g., the blood pump 204 is not properly mounted to the ventricular cuff (not shown). The one or more visual indicators 402 may be formed by filling machined wells in the cuff lock assembly 208 with colored silicone or the like. In other embodiments, the one or more visual indicators 402 are formed by selectively anodizing the visual indicator area in gold to provide contrast to the rest of the cuff lock assembly 208. In other embodiments, another component of a different color to the cuff lock assembly 208 may be attached (e.g., by press fitting or gluing a component that is flush or recessed relative to the sliding surfaces of the cuff lock assembly 208). In yet other embodiments, a colorized laser marking may be added that provides contrast to the cuff lock assembly 208 as a visual indicator. The one or more visual indicators 402 signal or otherwise alert a surgeon to reposition the cuff lock assembly 208 and try again. The one or more visual indicators 402 may also indicate to the surgeon that the cuff lock assembly 208 is in an unlocked position.

FIGS. 4B and 4C illustrate further views of the pump system in an unlocked position. Visible in these views, the blood pump 204 is spaced away from the ventricular cuff 302 and not properly seated. The inlet cannula 202 is insertable into the inlet cannula passage of the ventricular cuff 302. Further visible in these views, the flange 306 of the ventricular cuff 302 including the groove 308 are shown relative to the cuff lock assembly 208 in the retracted position. The cuff lock assembly 208 slides into the coupling mechanism (not shown) along direction 404. The coupling mechanism is encased by the blood pump 204 and the cuff lock cover 210 in these views. As the cuff lock assembly 208 is inserted, the cuff lock assembly 208 slides along the groove 308 of the flange 306 for securing the blood pump 204 to the ventricular cuff 302, to be described in further detail herein.

Figure 5:
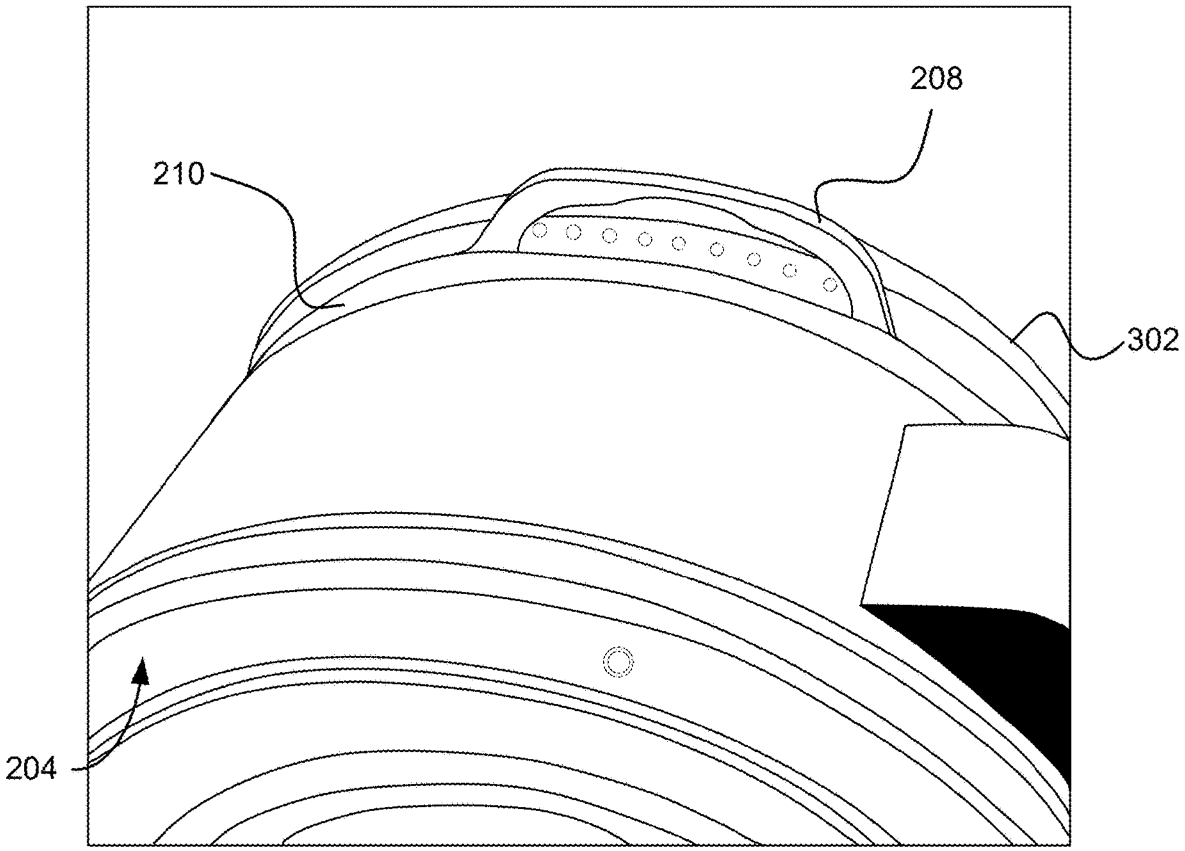
FIG. 5 illustrates a blood pump system in a locked configuration, in accordance with embodiments of the present disclosure.

FIG. 5 illustrates a blood pump system in a locked configuration. The description of system 10 and system 200 as described with respect to FIGS. 1-4C is relevant to the description of the exploded view described with respect to FIG. 5. Accordingly, similar components have similar numbering, form, and function unless otherwise noted herein. As shown, the cuff lock assembly 208 is fully inserted between the blood pump 204 and the cuff lock cover 210 for securing the blood pump 204 to the ventricular cuff 302. The one or more visual indicators are not visible in this view, further indicating that the cuff lock assembly 208 is secured and the blood pump 204 is properly seated relative to the ventricular cuff 302. One having ordinary skill in the art upon reading the present disclosure would appreciate that, based on the various embodiments described herein, if the blood pump 204 was not properly seated relative to the ventricular cuff 302, the cuff lock assembly 208 would not be able to advance into the locked configuration shown in FIG. 5 and the one or more visual indicators would be visible.

Various design implementations of the cuff lock assembly of the present invention are shown and described herein. Although each of the designs include a spring arm member for locking the cuff lock assembly in place, configurations without a spring arm member or having a different spring arm member than that shown and described herein are possible. Alternate embodiments can be configured that do not include the spring arm member and/or use alternate mechanisms for securing the cuff lock assembly in the engaged position.

Figure 6:
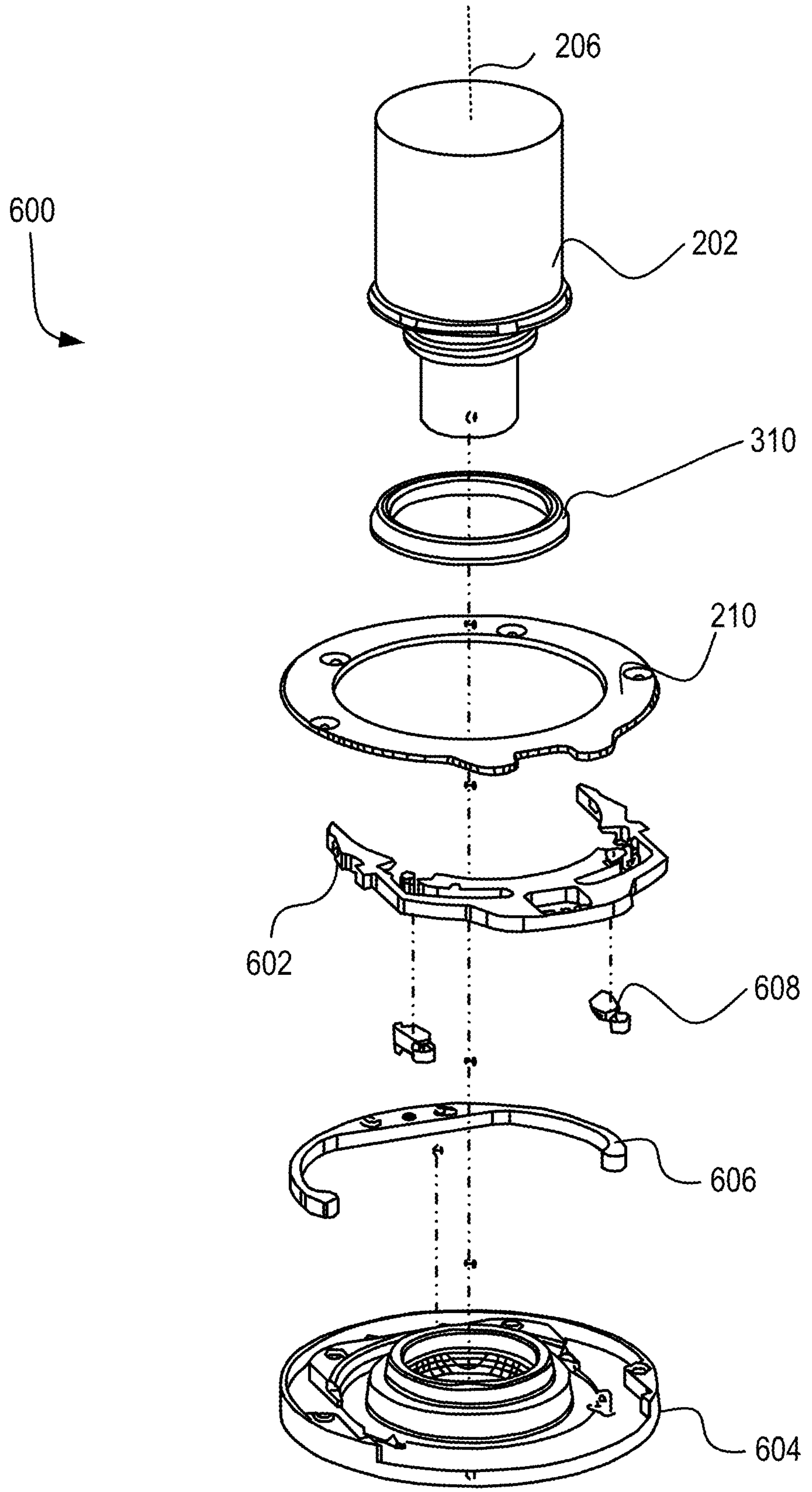
FIG. 6 is an exploded view of a cuff lock system, in accordance with embodiments of the present disclosure.

FIG. 6 is an exploded view of a cuff lock system. The description of system 10 and system 200 as described with respect to FIGS. 1-5 is relevant to the description of the exploded view described with respect to FIG. 6. Accordingly, similar components have similar numbering, form, and function unless otherwise noted herein. System 600 illustrates one embodiment of a cuff lock assembly including a cuff lock assembly 602 that is inserted into a coupling mechanism 604 and secured using a spring arm member 606. In particular, the coupling mechanism 604 includes a coupling mechanism housing including a cuff lock cover 210 that facilitates the alignment and translation of the cuff lock assembly 602 into the system 600. System 600 further includes one or more pivoting components 608 that enable the cuff lock assembly 602 to advance to a locked configuration when a blood pump including the coupling mechanism 604 is properly seated relative to a ventricular cuff. The one or more pivoting components 608 further prevent the cuff lock assembly from advancing to the locked configuration when the blood pump including the coupling mechanism 604 is not properly seated relative to the ventricular cuff. The one or more pivoting components 608 interact with the cuff lock assembly 602 as the cuff lock assembly 602 traverses from the retracted position to the locked position. Each component is described in further detail below.

Figure 7A:
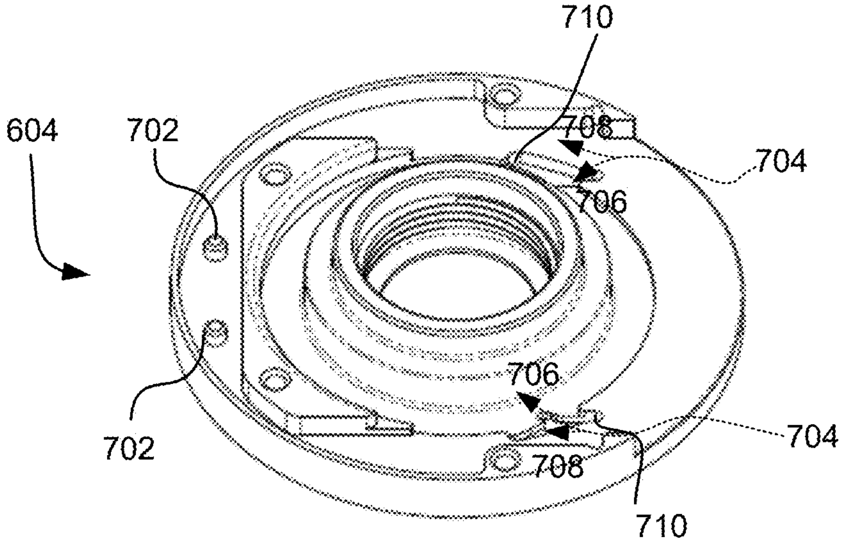
FIG. 7A is a perspective view of a coupling mechanism for a blood pump, in accordance with embodiments of the present disclosure.
Figure 7B:
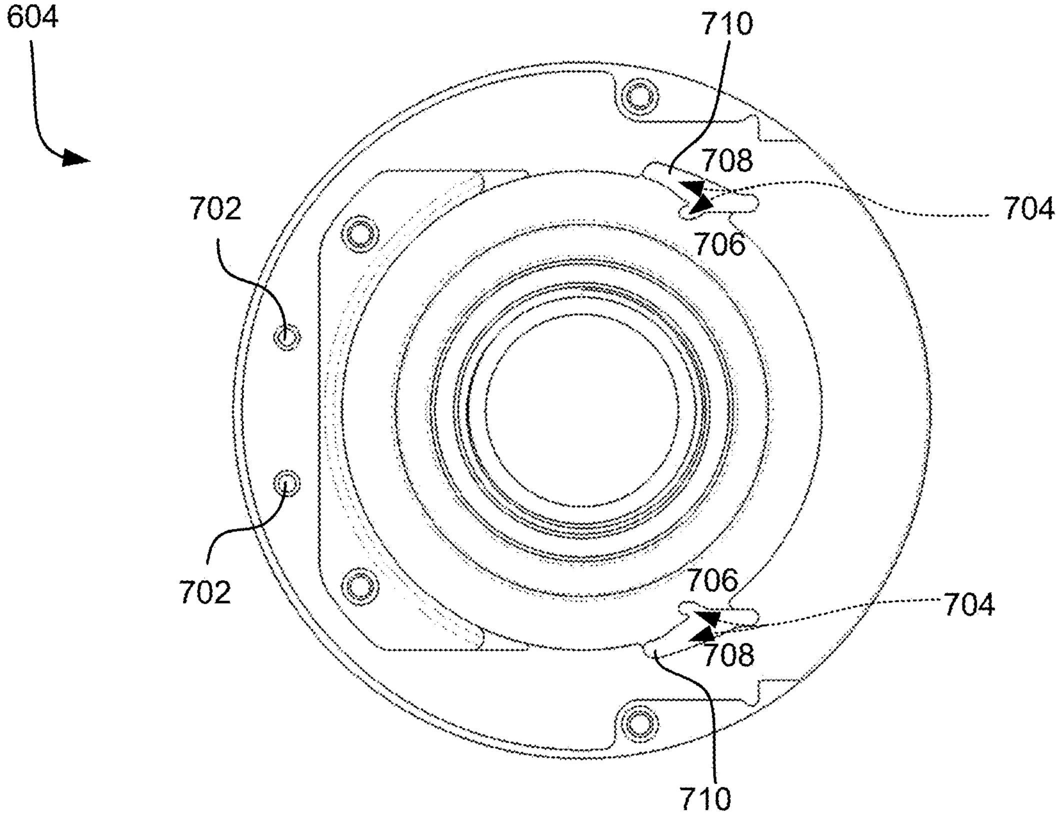
FIG. 7B is a top view of the coupling mechanism of FIG. 7A, in accordance with embodiments of the present disclosure.

FIG. 7A is a perspective view of a coupling mechanism for a blood pump. FIG. 7B is a top view of the coupling mechanism of FIG. 7A. The description of various systems as described with respect to FIGS. 1-6 is relevant to the description of FIGS. 7A and 7B. Accordingly, similar components have similar numbering, form, and function unless otherwise noted herein. The coupling mechanism 604 includes one or more protrusions 702 for securing a spring arm member (such as spring arm member 606) in position. The coupling mechanism 604 defines cuff lock passages 704. Cuff lock arms of cuff lock assembly 602 are slidably disposed within the cuff lock passages 704 defined by the coupling mechanism 604. Depending on the positioning of one or more pivoting components and whether the blood pump is properly seated relative to the ventricular cuff, the cuff lock arms (e.g., one or more pivoting components of the cuff lock arms) travel a first direction 706 to a locked position or a second direction 708 to a lockout position, to be described in further detail below. The coupling mechanism 604 further defines one or more detents 710 that direct corresponding one or more pivoting components between a first position and a second position, to be described in further detail below. In various embodiments, the one or more pivoting components each include at least one pivot (as shown in FIG. 9D) that are captured by posts 808 of the cuff lock assembly 602 (described with respect to FIGS. 8A-8C below). Further, the one or more pivoting components each include at least one post (as shown in FIG. 9D) that interact with the one or more detents 710 of the coupling mechanism 604. This interaction governs the length of the travel of the cuff lock assembly 602 along the first direction 706 or the second direction 708. A first position of the one or more pivoting components corresponds to the locked position or configuration of the cuff lock assembly. A second position of the one or more pivoting components corresponds to the lockout position or configuration of the cuff lock assembly.

Figure 8A:
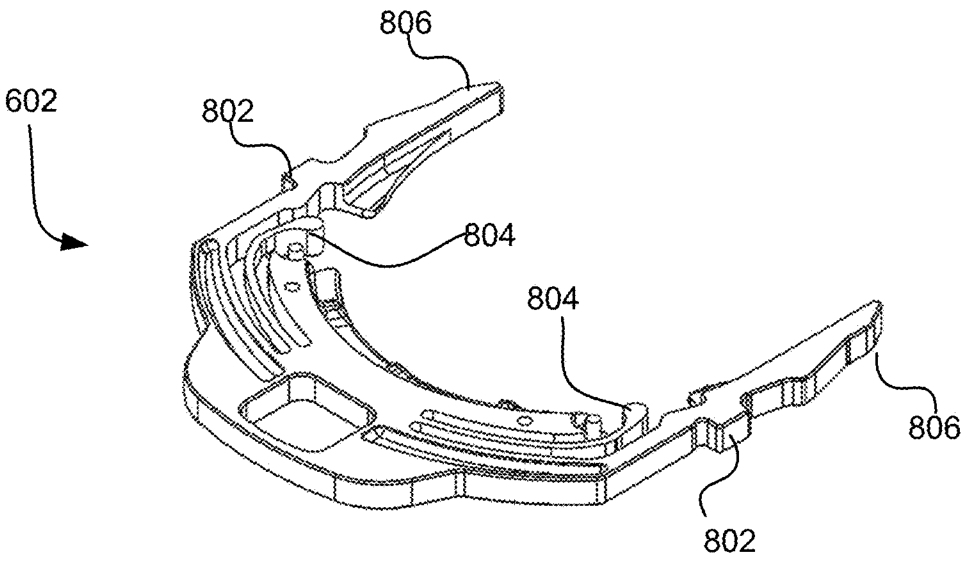
FIG. 8A is a perspective view of a cuff lock assembly, in accordance with embodiments of the present disclosure.
Figure 8B:
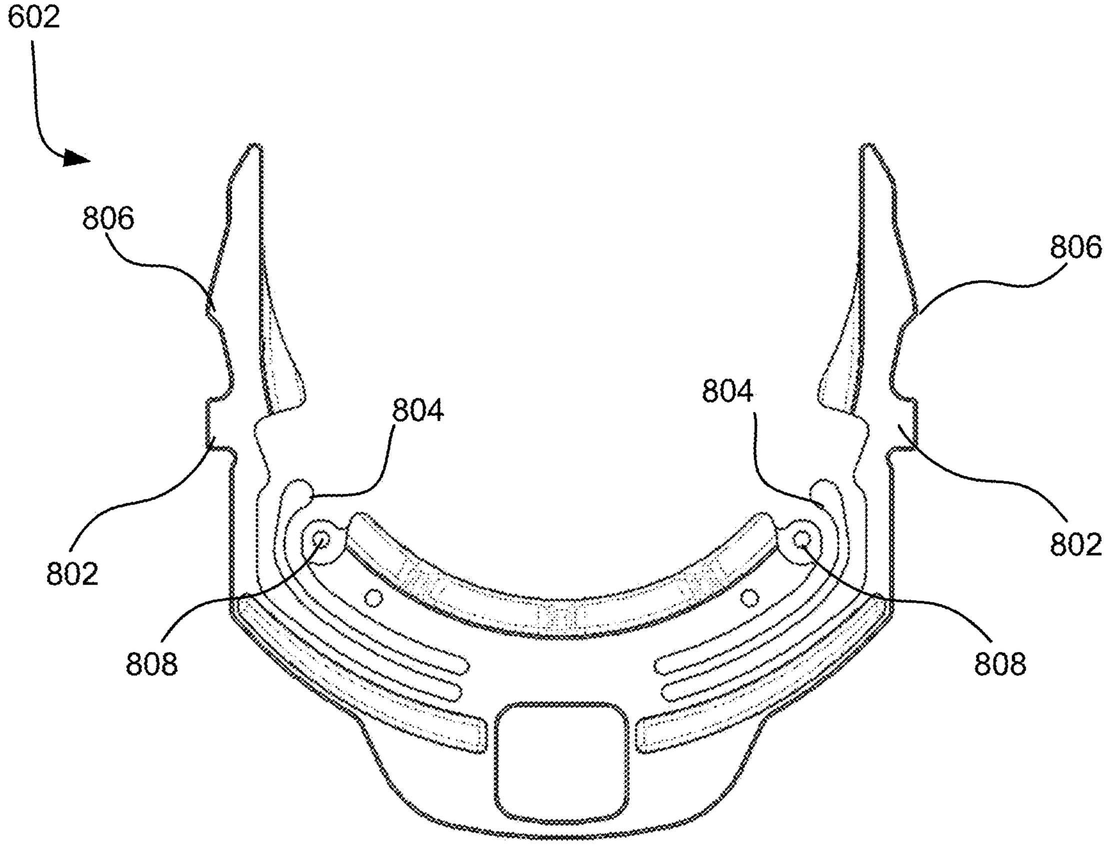
FIG. 8B is a bottom view of the cuff lock assembly of FIG. 8A, in accordance with embodiments of the present disclosure.
Figure 8C:
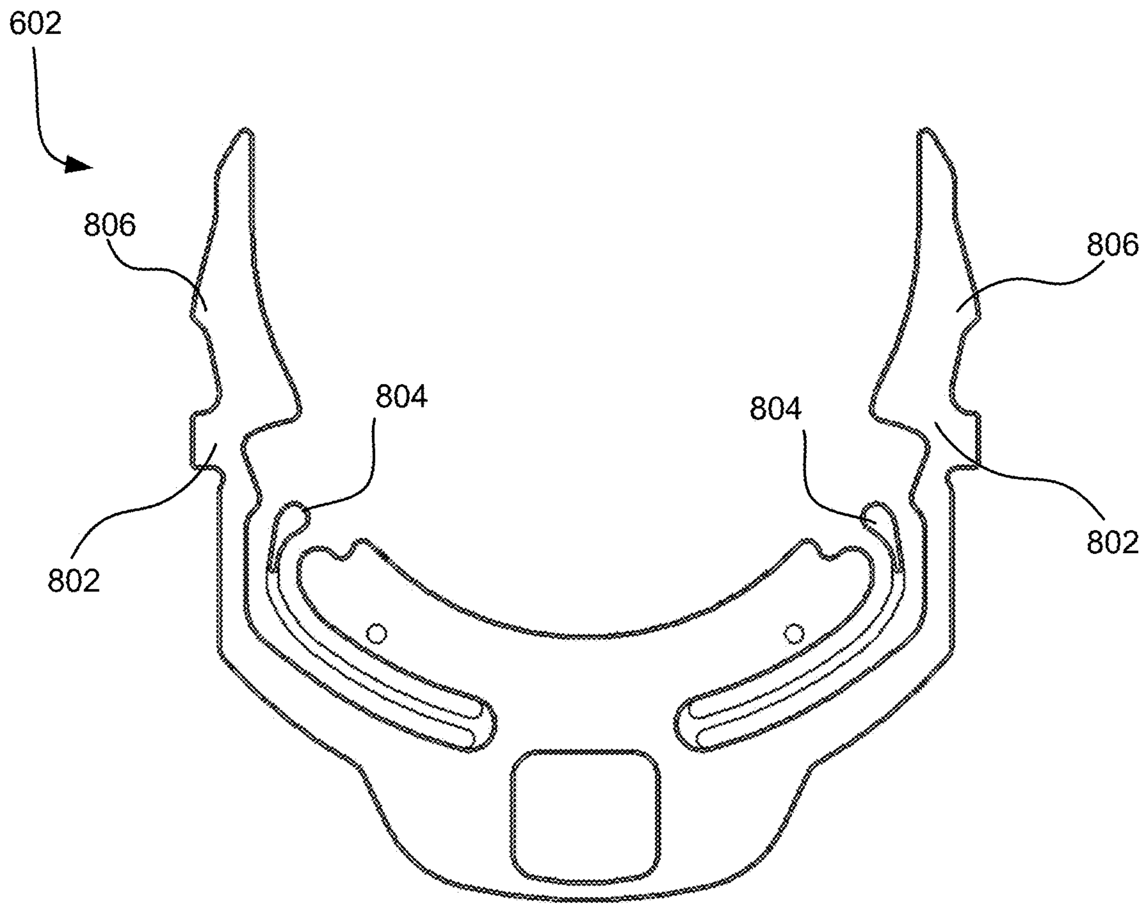
FIG. 8C is a top view of the cuff lock assembly of FIG. 8A, in accordance with embodiments of the present disclosure.

FIG. 8A is a perspective view of a cuff lock assembly. FIG. 8B is a bottom view of the cuff lock assembly of FIG. 8A. FIG. 8C is a top view of the cuff lock assembly of FIG. 8A. The description of various systems as described with respect to FIGS. 1-7B is relevant to the description of FIGS. 8A-8C. The cuff lock assembly 602 is repositionable relative to the coupling mechanism between a retracted position and an engaged (e.g., locked) position. For example, the cuff lock assembly 602 in the retracted position accommodates insertion of the inlet cannula into the inlet cannula passage to mount the blood pump onto the ventricular cuff into a mounted configuration (e.g., a properly seated configuration).

The cuff lock assembly 602 includes cuff lock arms 802 that are slidably disposed within cuff lock passages 704 defined by the coupling mechanism 604 described with respect to FIGS. 7A and 7B. The cuff lock arms 802 are configured to extend over the outward facing circumferential flange 306 of the ventricular cuff 302 as shown at least in FIGS. 3, 4B, and 4C. Furthermore, the cuff lock arms 802 are configured to extend over the outward facing circumferential flange 306 of the ventricular cuff 302 in the mounted configuration when the cuff lock assembly 602 is in the engaged position to secure the blood pump 204 to the ventricular cuff 302. According to various embodiments, the cuff lock assembly 602 further includes one or more spring arms 804 that interact with the one or more pivoting members of the coupling mechanism. According to at least some embodiments, the spring arms 804 are thicker at the free end to prevent twisting in the channel while flexing. The thickness and height of the spring arms 804 can be tuned to adjust the amount of lateral force applied to the pivots. According to further embodiments, the cuff lock arms 802 include one or more ridges 806 for engaging with and securing the cuff lock arms 802 relative to a spring arm member within the coupling mechanism, to be described in further detail below.

As shown in FIG. 8B, the bottom surface of the cuff lock assembly 602 includes one or more posts 808 that couple to corresponding pivots of the one or more pivoting components 608 as the cuff lock arms 802 slide along the cuff lock passages 704 defined by the coupling mechanism 604 described with respect to FIGS. 7A and 7B.

Figures 9A, 9B, 9C:
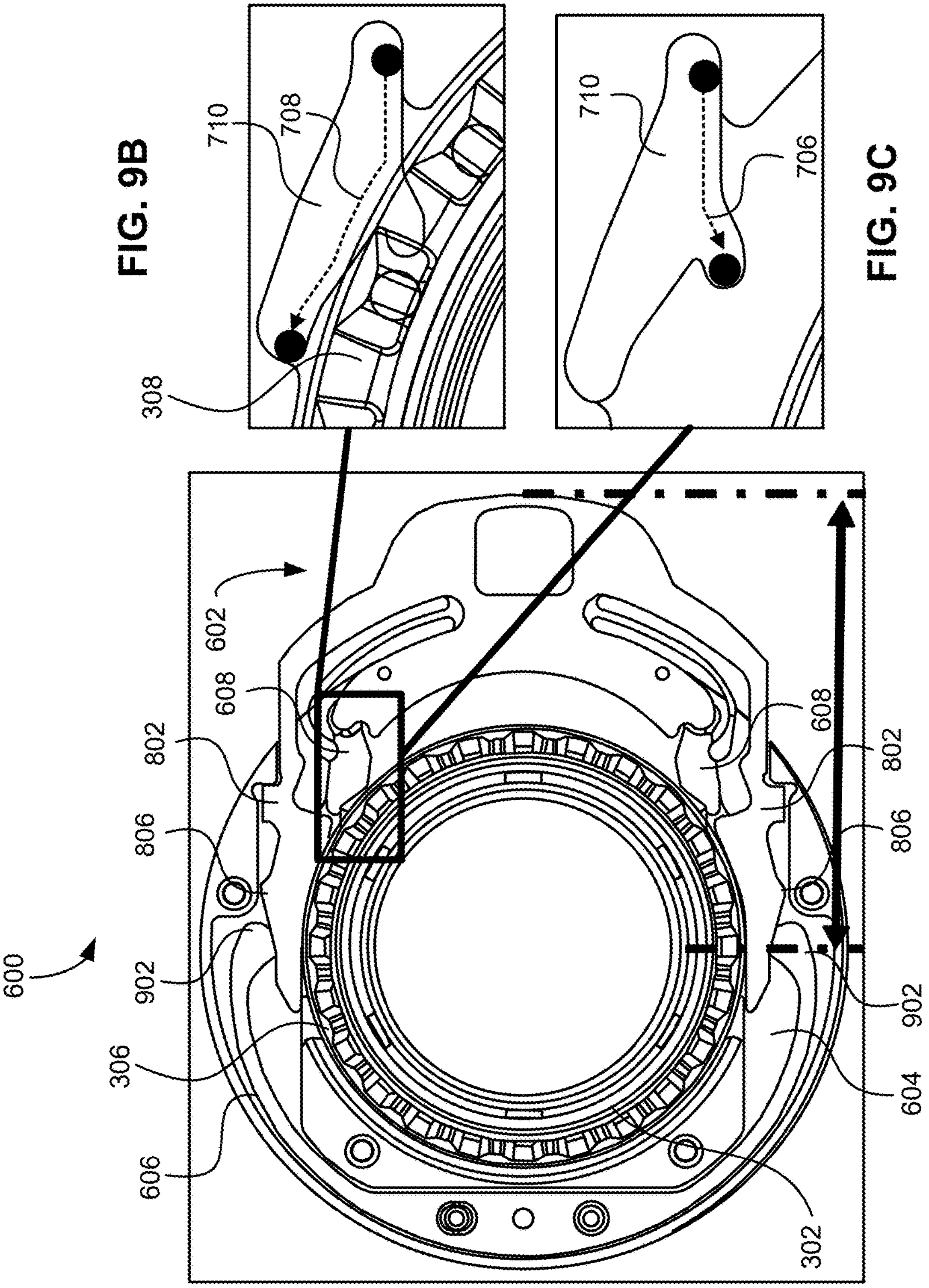
FIG. 9A is a top view of a cuff lock system in a retracted configuration, in accordance with embodiments of the present disclosure.
FIG. 9B is an inset of the cuff lock system of FIG. 9A, in accordance with embodiments of the present disclosure.
FIG. 9C illustrates the lockout path, in accordance with embodiments of the present disclosure.
Figure 9D:
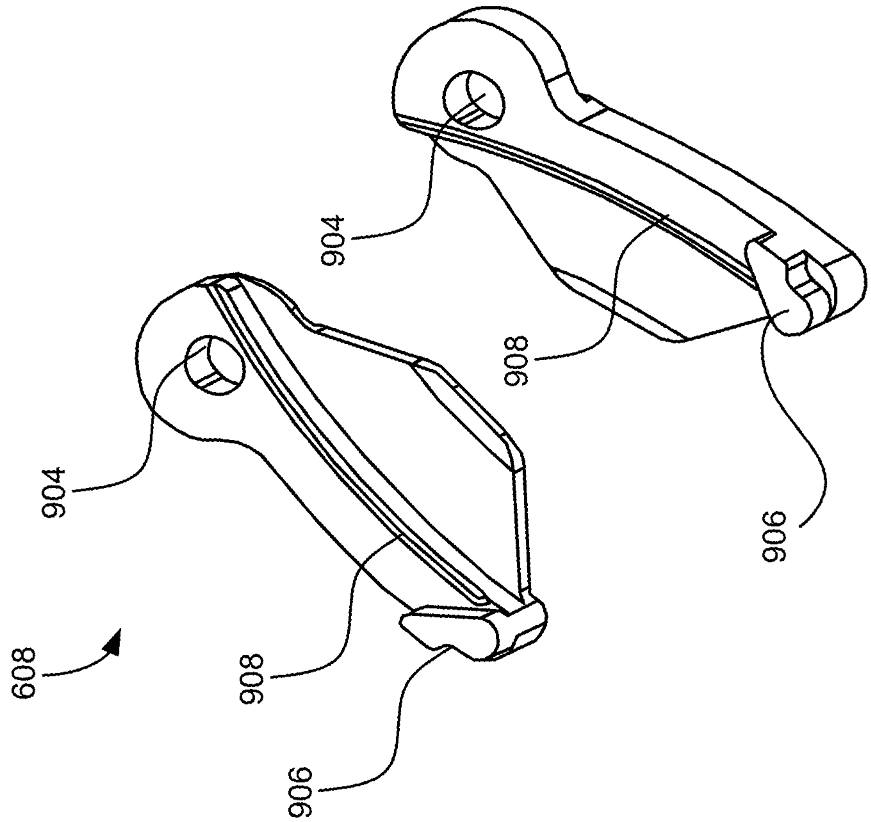
FIG. 9D is a pair of pivoting components of FIG. 9A, in accordance with embodiments of the present disclosure.
Figure 9G:
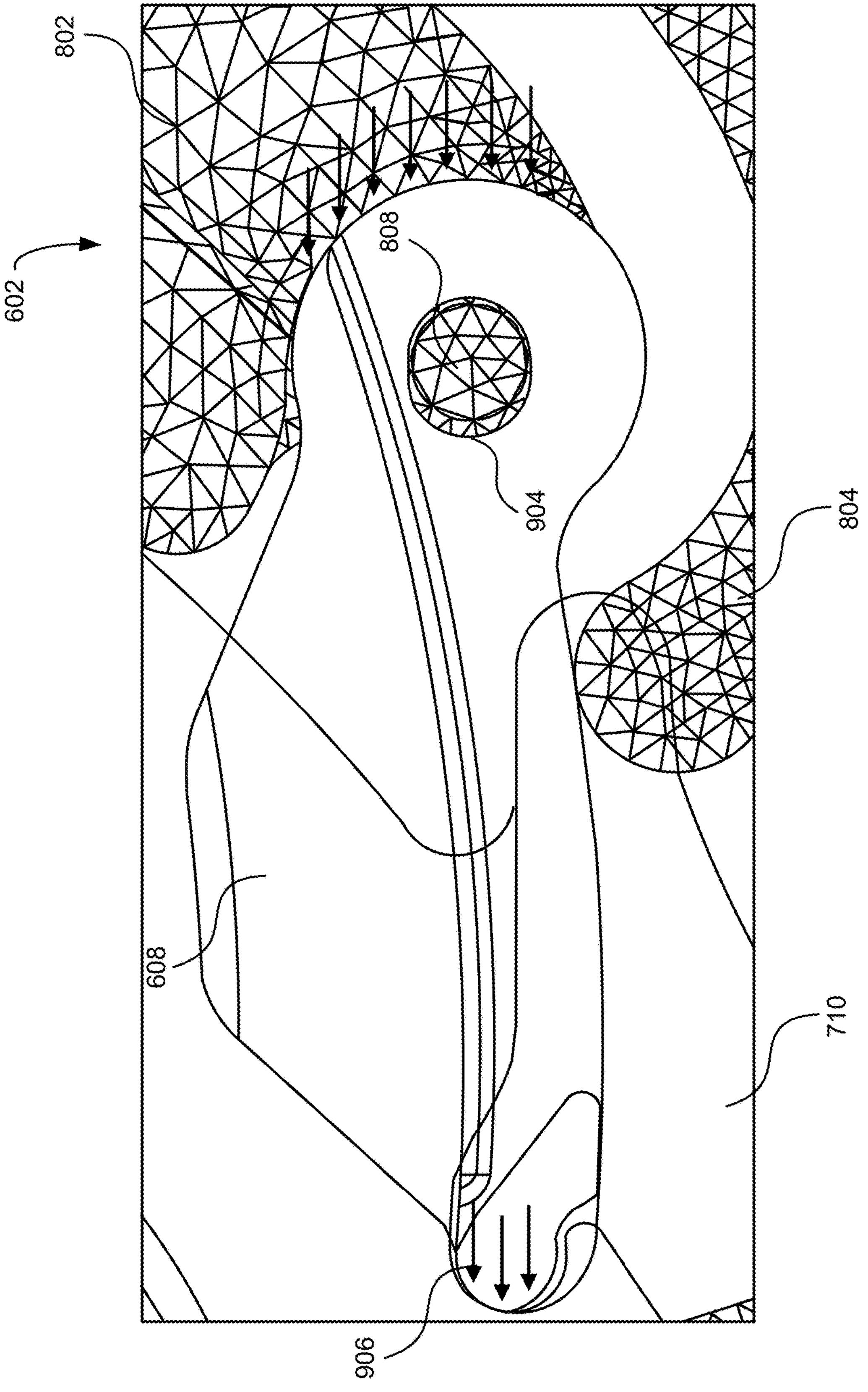
FIG. 9G illustrates compression forces of the cuff lock system in the lockout configuration of FIG. 9E, in accordance with embodiments of the present disclosure.

FIG. 9A is a top view of a cuff lock system in a retracted configuration. FIG. 9B is an inset of the cuff lock system of FIG. 9A. FIG. 9C illustrates the lockout path. FIG. 9D is a pair of pivoting components of FIG. 9A. FIG. 9E is a top view of a cuff lock system in a lockout configuration. FIG. 9F is an inset of the cuff lock system of FIG. 9D. FIG. 9G illustrates compression forces of the cuff lock system in the lockout configuration of FIG. 9E. The description of various systems as described with respect to FIGS. 1-8C is relevant to the description of FIGS. 9A-9G. Accordingly, similar components have similar numbering, form, and function unless otherwise noted herein. As shown in FIG. 9A, the spring arm member 606 includes flexible arms 902 configured to engage the cuff lock arms 802 of the cuff lock assembly 602. In particular, the flexible arms 902 of the spring arm member 606 are configured to wrap around and secure the one or more ridges 806 of the cuff lock arms 802 of the cuff lock assembly 602 in a locked position and inhibit repositioning of the cuff lock arms 802 relative to the coupling mechanism.

Figure 10A:
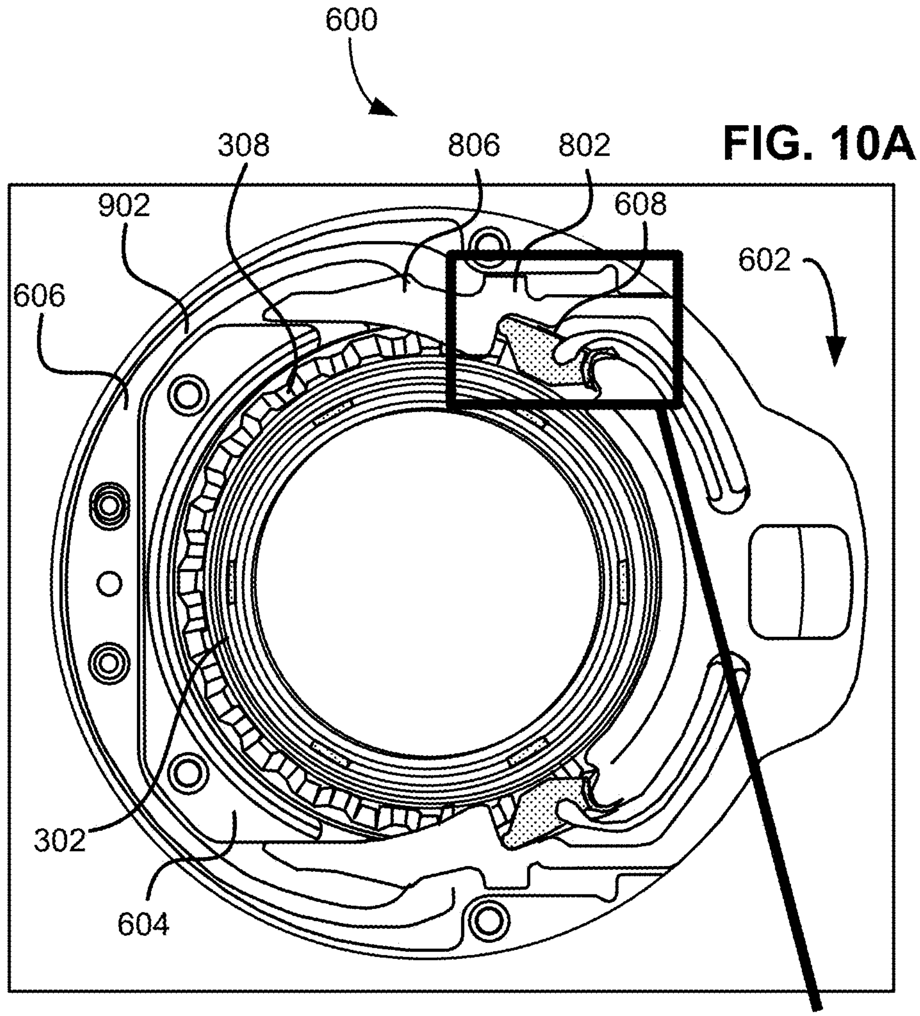
FIG. 10A is a top view of a cuff lock system in a locked configuration, in accordance with embodiments of the present disclosure.
Figure 10B:
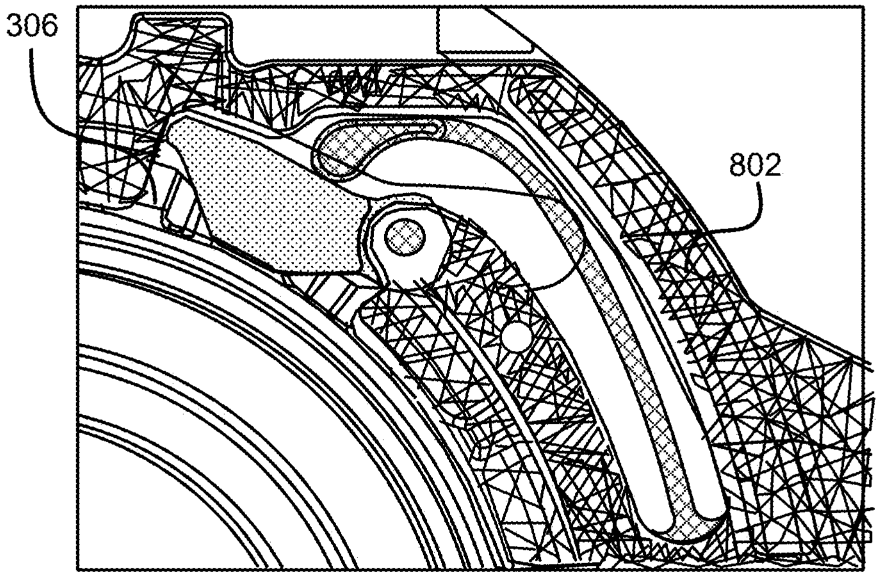
FIG. 10B is an inset of the cuff lock system of FIG. 10A, in accordance with embodiments of the present disclosure.

As shown in FIG. 9A, the cuff lock assembly 602 is in a retracted position and the ventricular cuff 302 is positioned such that the flange 306 is seated relative to the blood pump (e.g., the coupling mechanism 604 of the blood pump). In this position, the flange 306 abuts against the one or more pivoting components 608 and, as the cuff lock assembly 602 is advanced toward the locked position, the flange 306 directs the one or more pivoting components 608 radially outward to the first position as shown in FIGS. 10A and 10B. FIG. 9B further illustrates how the presence of the flange 306 directs the pivots 906 of the pivoting components through the detents of the coupling mechanism 604 such that the pivots 906 travel along the first direction 706 toward the locked configuration. In contrast, when the flange 306 is not present (e.g., when the ventricular cuff 302 is not present or not properly seated), the pivots of the pivoting components travel by default through the detents of the coupling mechanism 604 such that the pivots 906 travel along the second direction 708 toward the lockout position configuration. According to some embodiments, the cuff lock arms 802 may flex and apply an inward force to the pivots 906 in contact with the detents 710 and the outer edge of the flange 306 when the cuff lock assembly 602 is properly seated. When the cuff lock arms 802 are spring loaded inwards, the pivots 906 are prevented from floating between the detents 710 of the first direction 706 and the second direction 708.

FIG. 9D shows a bottom view of the one or more pivoting components 608. As shown, the one or more pivoting components 608 each include a pivot 906. The pivot slots 904 insert into the posts 808 of the cuff lock assembly 602, capturing the pivoting components 608 between the coupling mechanism 604 and the cuff lock assembly 602. Further shown, the one or more pivoting components 608 each include a pivot 906 and/or a sliding feature 908 that engage with and slide along the detents 710 of the coupling mechanism 604.

FIG. 9E is a top view of a cuff lock system in a lockout configuration. FIG. 9F is an inset of the cuff lock system of FIG. 9D. As shown in FIG. 9E, when the flange 306 of the ventricular cuff 302 is not present, the spring arms 804 of the cuff lock assembly 602 keep the one or more pivoting components 608 on the lockout track as shown in FIG. 9C. The spring arms 804 of the cuff lock assembly 602 further interact with the one or more pivoting components 608 preventing the cuff lock assembly 602 from advancing toward the spring arm member 606 and the locked position. FIG. 9G illustrates compression forces of the cuff lock system in the lockout configuration of FIG. 9E. The geometry of the one or more pivoting components 608 is designed to withstand the compressive forces applied by the surgeon during lockout. This is especially important if the surgeon forcefully pushes the cuff lock assembly 602 radially in toward the center of the blood pump expecting the cuff lock assembly 602 to lock into place. The bearing surfaces of this force include the free end of the one or more pivoting components 608 against the end of the detents 710. On the opposite end of the one or more pivoting components 608, the length of the pivot slot 904 ensures that the compression forces are transferred to the outer diameter of the portion of the cuff lock arm 802 having the post 808 and the interfacing surface of the cuff lock assembly 602, rather than against the small, more fragile post 808 machined into the cuff lock assembly 602 that keeps the one or more pivoting components 608 captive in the cuff lock assembly 602. In various embodiments, the length of the pivot slot 904 is long enough along the direction of compression to avoid applying force to 808 in a lockout configuration.

FIG. 10A is a top view of a cuff lock system in a locked configuration. FIG. 10B is an inset of the cuff lock system of FIG. 10A. The description of various systems as described with respect to FIGS. 1-9G is relevant to the description of FIGS. 10A-10B. Accordingly, similar components have similar numbering, form, and function unless otherwise noted herein. As shown in FIG. 10A, when the ventricular cuff 302 is present and the flange 306 is properly seated, the flange 306 blocks the one or more pivoting components 608 from traveling along the medial wall of the detents 710 and into the first position (e.g., resulting in a locked position). Accordingly, the cuff lock arms 802 are able to travel along the coupling mechanism 604 such that the flexible arms 902 of the spring arm member 606 extend around the ridges 806 of the cuff lock arms 802 and secure the cuff lock assembly 602 in the locked position. In various embodiments, the cuff lock assembly 602 is not repositionable once the cuff lock assembly 602 is in the locked position at shown in FIGS. 10A-10B. The steep backside angle of the ridge 806 prevents the cuff lock assembly 602 from retracting without the use of an additional tool (not shown).

Figure 11A:
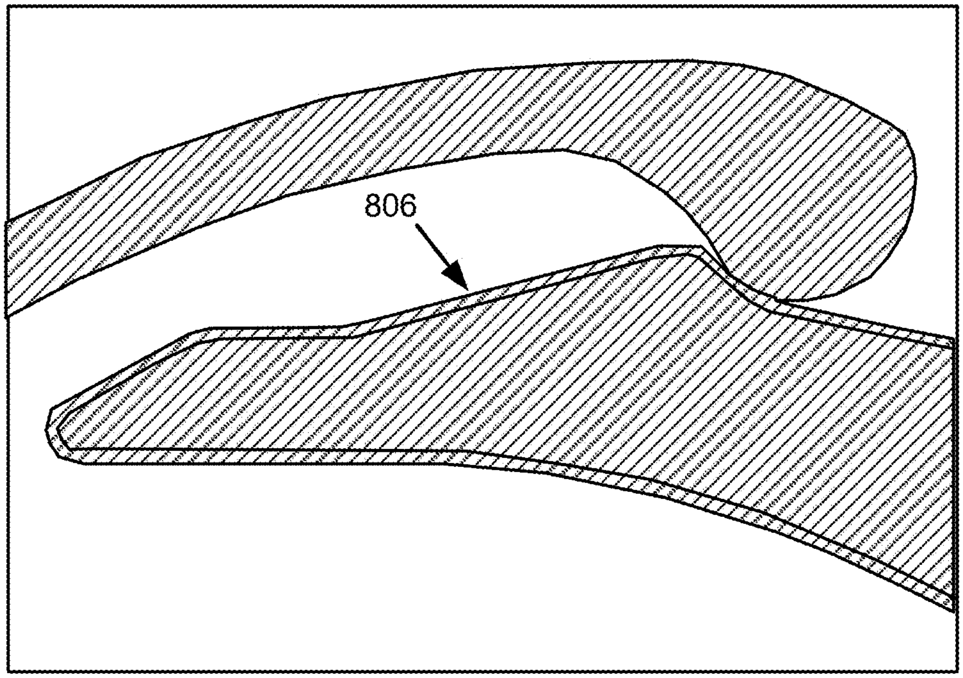
FIG. 11A is a cuff lock arm ridge, in accordance with embodiments of the present disclosure.
Figure 11B:
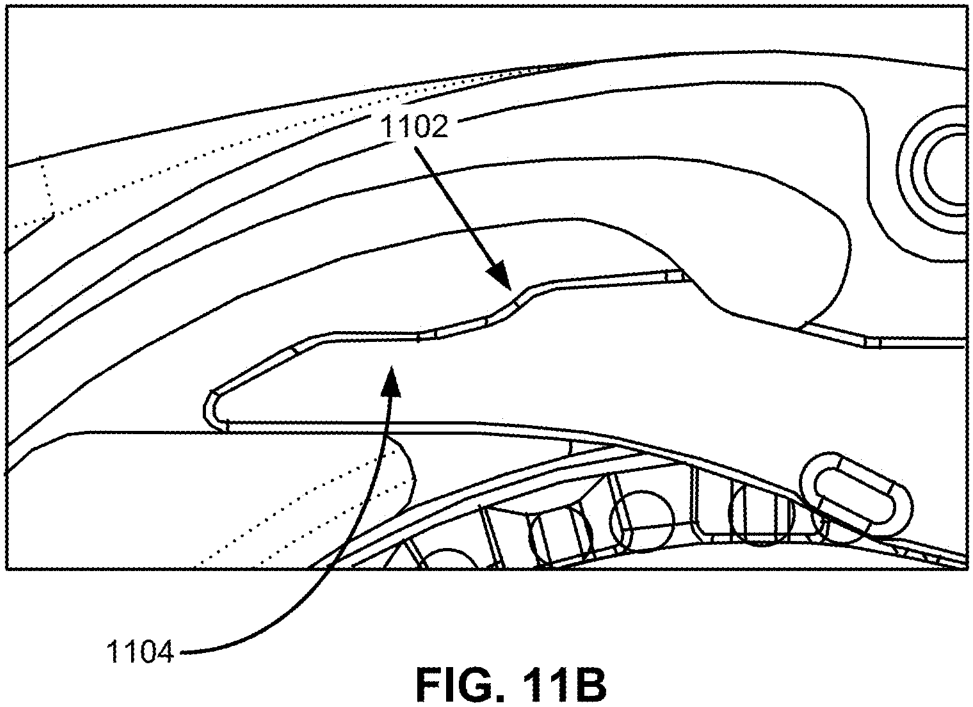
FIG. 11B is an alternative cuff lock arm ridge, in accordance with embodiments of the present disclosure.

FIG. 11A is a cuff lock arm ridge. FIG. 11B is an alternative cuff lock arm ridge. The description of various systems as described with respect to FIGS. 1-10B is relevant to the description of FIGS. 11A-11B. Accordingly, similar components have similar numbering, form, and function unless otherwise noted herein. FIG. 11A illustrates the cuff lock arm ridge 806 as used throughout the previous figures. FIG. 11B illustrates an alternative cuff lock ridge 1102 having a sharp jog 1104 that provides more pronounced tactile feedback to indicate that the cuff lock assembly has entered the retracted position. The alternative cuff lock ridge 1102 may be used in any of the embodiments of a cuff lock assembly described herein. The alternative cuff lock ridge 1102 may also reduce the occurrence of inadvertently pushing the cuff lock assembly from the retracted position to the locked or lockout position by increasing the initial force required to push it in radially. According to various embodiments, the slope and contours of the profile can be adjusted beyond what is shown in FIGS. 11A and 11B to fine tune the forces encountered when actuating the cuff lock assembly between retracted and locked/lockout positions (bidirectionally).

Figure 12A:
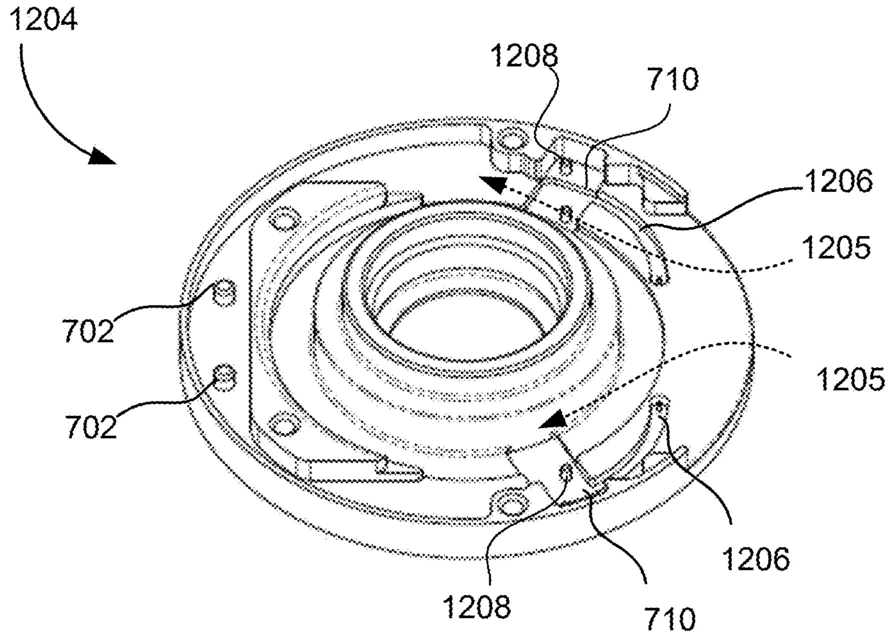
FIG. 12A is a perspective view of a coupling mechanism for a blood pump, in accordance with embodiments of the present disclosure.
Figure 12B:
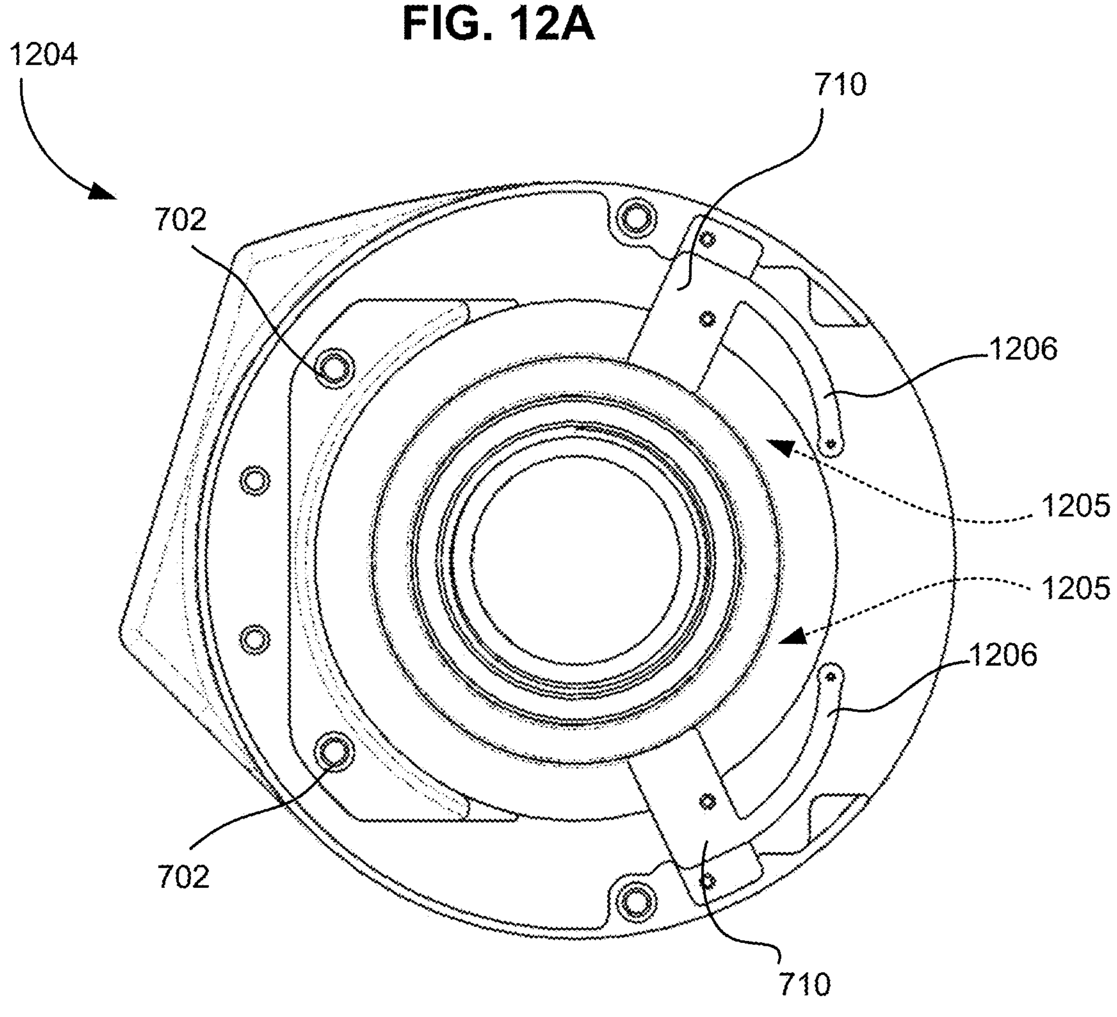
FIG. 12B is a top view of the coupling mechanism of FIG. 12A, in accordance with embodiments of the present disclosure.

FIG. 12A is a perspective view of a coupling mechanism for a blood pump. FIG. 12B is a top view of the coupling mechanism of FIG. 12A. The description of various systems as described with respect to FIGS. 1-11B is relevant to the description of FIGS. 12A-12B. Accordingly, similar components have similar numbering, form, and function unless otherwise noted herein. The coupling mechanism 1204 includes one or more protrusions 702 for securing a spring arm member (such as spring arm member 606) in position. The coupling mechanism 1204 defines cuff lock passages 1205. Cuff lock arms of cuff lock assembly 1202 are slidably disposed within the cuff lock passages 1205 defined by the coupling mechanism 1204. The coupling mechanism 1204 further defines one or more detents 710 that direct the corresponding one or more stop components between a first position and a second position, to be described in further detail below. In various embodiments, the one or more stop components each include at least one aperture that a post 1208 of the coupling mechanism 1204 slides along. The one or more stop components each include a stop ledge that directs or stops the cuff lock arms 802 of the cuff lock assembly 1202. The coupling mechanism 1204 further includes slots 1206 for one or more springs that direct the stop components between the first position and the second position. This interaction governs the length of travel of the cuff lock assembly 1202 along cuff lock passages 1205. A first position of the one or more stop components corresponds to the locked position or configuration of the cuff lock assembly. A second position of the one or more stop components corresponds to the lockout position or configuration of the cuff lock assembly.

Figure 13A:
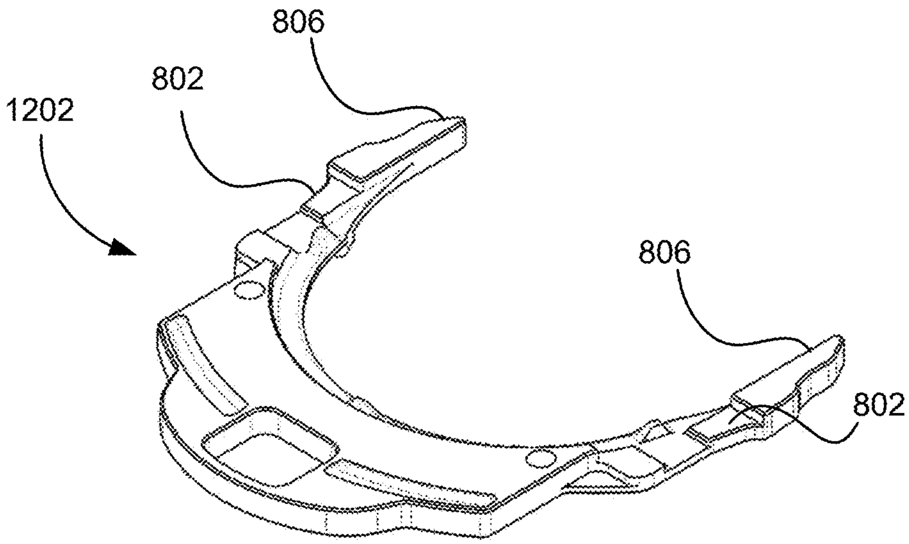
FIG. 13A is a perspective view of a cuff lock assembly, in accordance with embodiments of the present disclosure.
Figure 13B:
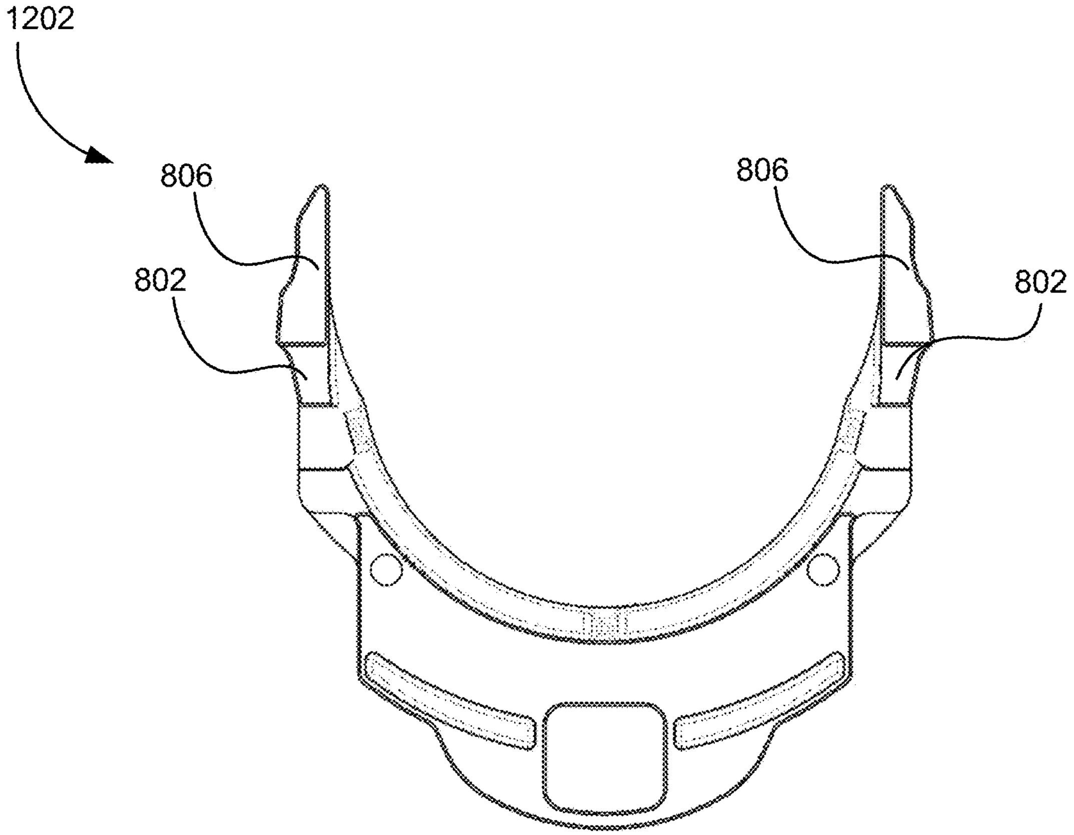
FIG. 13B is a bottom view of the cuff lock assembly of FIG. 13A, in accordance with embodiments of the present disclosure.
Figure 13C:
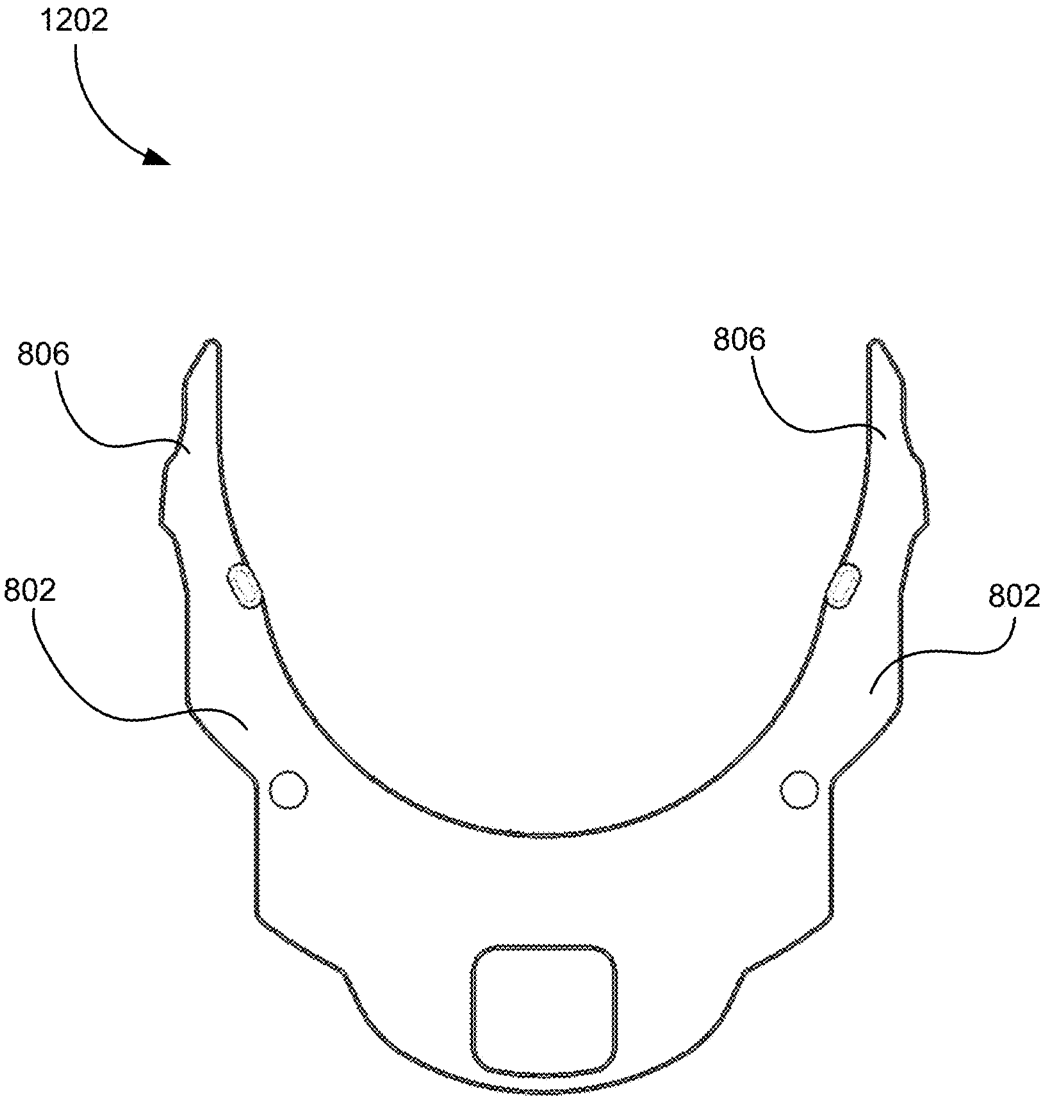
FIG. 13C is a top view of the cuff lock assembly of FIG. 13A, in accordance with embodiments of the present disclosure.

FIG. 13A is a perspective view of a cuff lock assembly. FIG. 13B is a bottom view of the cuff lock assembly of FIG. 13A. FIG. 13C is a top view of the cuff lock assembly of FIG. 13A. The description of various systems as described with respect to FIGS. 1-12B is relevant to the description of FIGS. 13A-13C. Accordingly, similar components have similar numbering, form, and function unless otherwise noted herein. The cuff lock assembly 1202 is repositionable relative to the coupling mechanism between a retracted position and an engaged (e.g., locked) position. For example, the cuff lock assembly 1202 in the retracted position accommodates insertion of the inlet cannula into the inlet cannula passage to mount the blood pump onto the ventricular cuff into a mounted configuration (e.g., a properly seated configuration).

The cuff lock assembly 1202 includes cuff lock arms 802 that are slidably disposed within cuff lock passages 1205 defined by the coupling mechanism 1204 described with respect to FIGS. 12A and 12B. The cuff lock arms 802 are configured to extend over the outward facing circumferential flange 306 of the ventricular cuff 302 as shown at least in FIGS. 3, 4B, and 4C. Furthermore, the cuff lock arms 802 are configured to extend over the outward facing circumferential flange 306 of the ventricular cuff 302 in the mounted configuration when the cuff lock assembly 1202 is in the engaged position to secure the blood pump 204 to the ventricular cuff 302. According to further embodiments, the cuff lock arms 802 include one or more ridges 806 for engaging with and securing the cuff lock arms 802 relative to a spring arm member 606 within the coupling mechanism 1204 similarly to the cuff lock assembly 602 described in detail above.

Figure 14A:
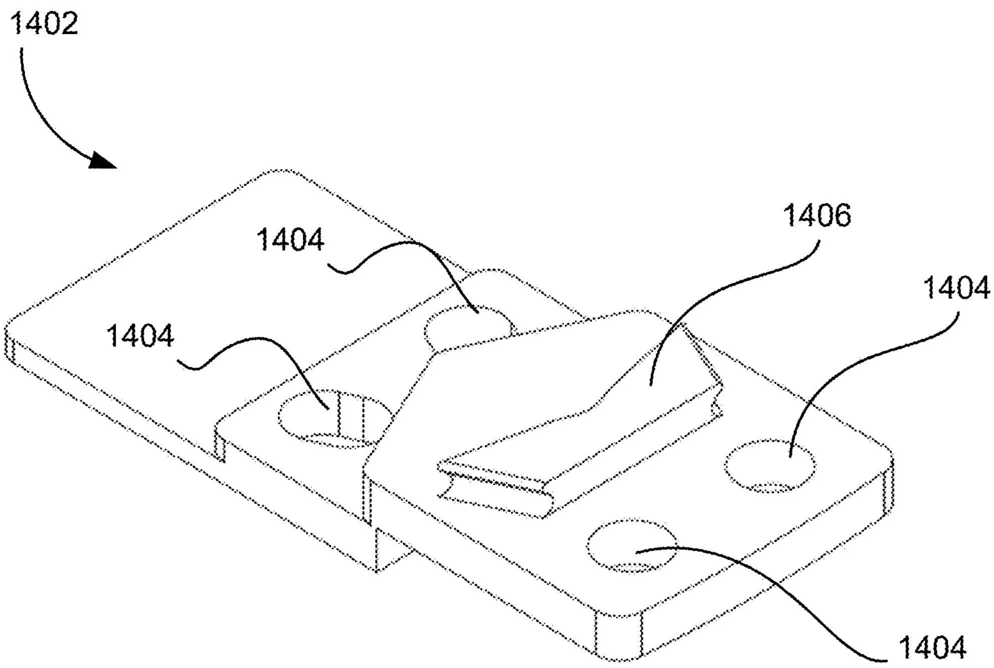
FIG. 14A is a perspective view of a stop component, in accordance with embodiments of the present disclosure.
Figure 14B:
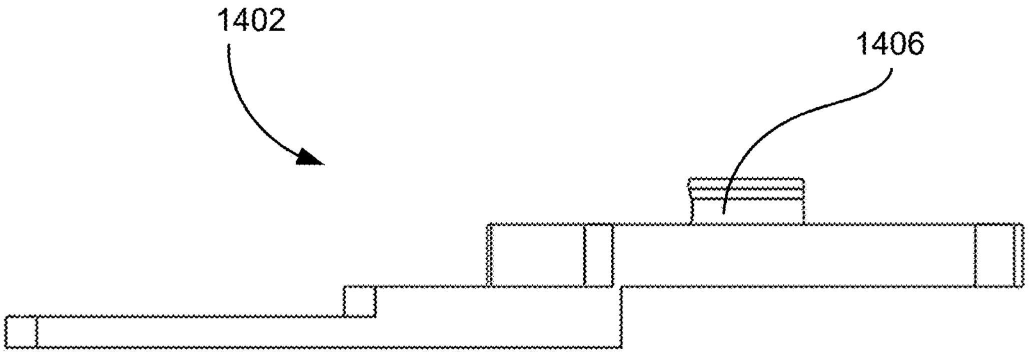
FIG. 14B is a side view of a stop component, in accordance with embodiments of the present disclosure.

FIG. 14A is a perspective view of a stop component. FIG. 14B is a side view of a stop component. The description of various systems as described with respect to FIGS. 1-13C is relevant to the description of FIGS. 14A-14B. Accordingly, similar components have similar numbering, form, and function unless otherwise noted herein. Each stop component 1402 interacts with a curved spring positioned in the slots 1206 of the coupling mechanism 1204. The apertures 1404 of the stop components 1402 are held captive by posts 1208 machined into the coupling mechanism 1204.

Figure 15A:
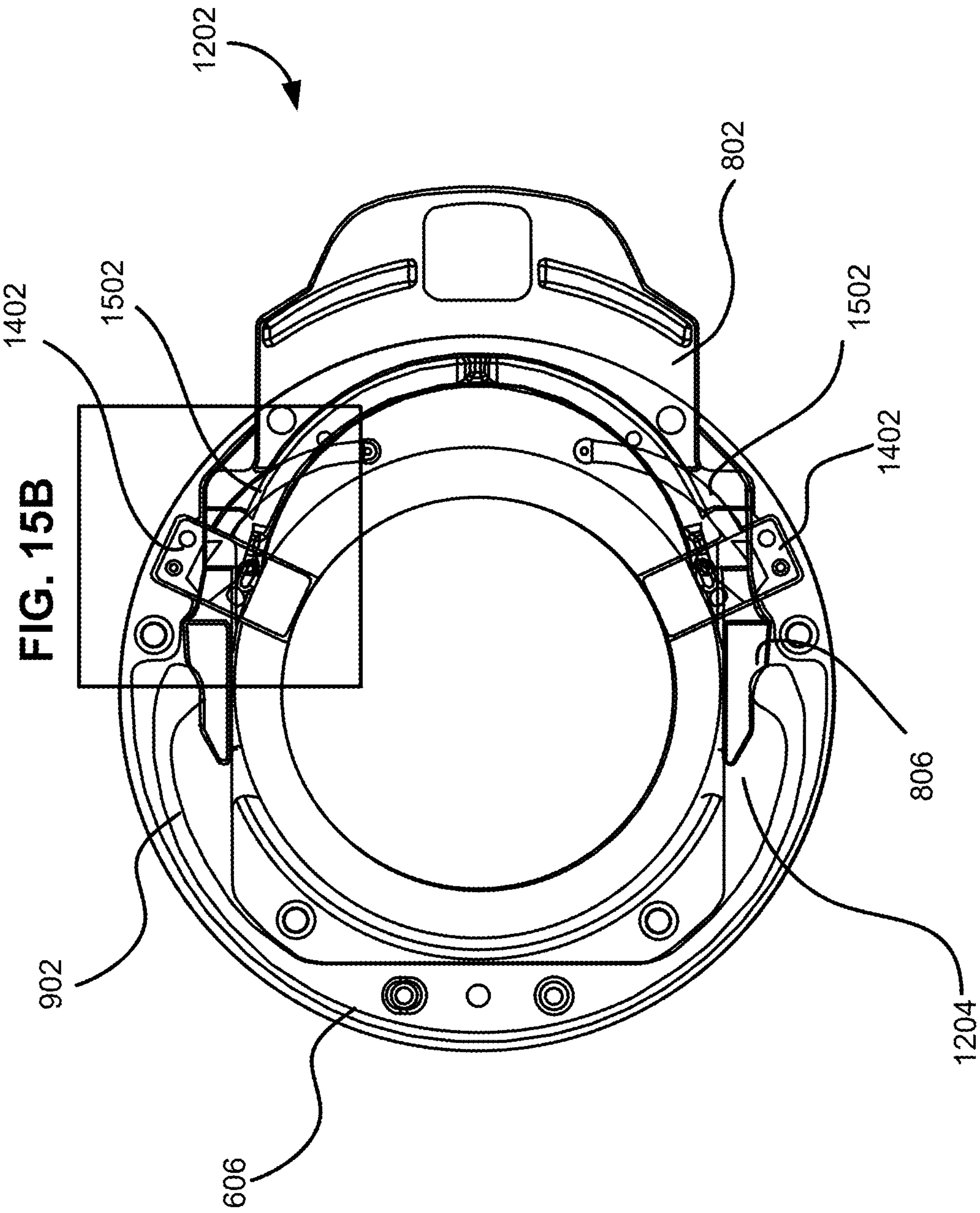
FIG. 15A is a top view of a cuff lock system in a retracted configuration, in accordance with embodiments of the present disclosure.
Figure 15B:
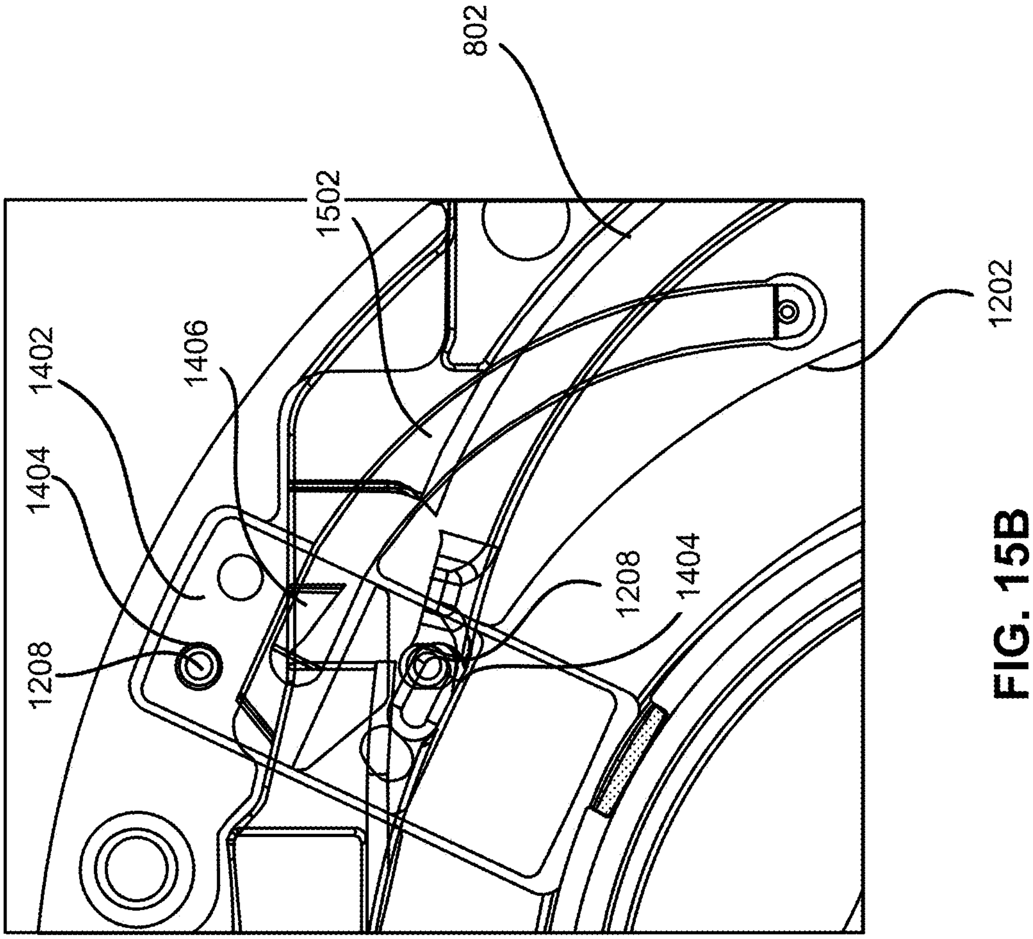
FIG. 15B is an inset of the cuff lock system of FIG. 15A, in accordance with embodiments of the present disclosure.

FIG. 15A is a top view of a cuff lock system in a retracted configuration. FIG. 15B is an inset of the cuff lock system of FIG. 15A. The description of various systems as described with respect to FIGS. 1-14B is relevant to the description of FIGS. 15A-15B. Accordingly, similar components have similar numbering, form, and function unless otherwise noted herein. As shown in FIG. 15A, the spring arm member 606 includes flexible arms 902 configured to engage the cuff lock arms 802 of the cuff lock assembly 1202. In particular, the flexible arms 902 of the spring arm member 606 are configured to wrap around and secure the one or more ridges 806 of the cuff lock arms 802 of the cuff lock assembly 1202 in a locked position and inhibit repositioning of the cuff lock arms 802 relative to the coupling mechanism 1204. As shown in FIG. 15A, the cuff lock assembly 1202 is in a retracted position. The coupling mechanism 1204 may include springs 1502. In various embodiments, the springs 1502 can be of various shapes and materials, fine-tuned to apply enough vertical force to ensure the stop components are proud in the retracted and lockout positions, but also not too high to significantly increase the amount of force required to fully seat the pump onto the cuff. In some embodiments, an elastomeric material may be applied underneath the stop component to act as a spring. As further shown in FIG. 15B, the posts 1208 machined into the coupling mechanism 1204 extend through apertures 1404 of the stop component 1402. Furthermore, the spring 1502 relative to the stop ledge 1406 is also illustrated in the retracted position.

Figure 16A:
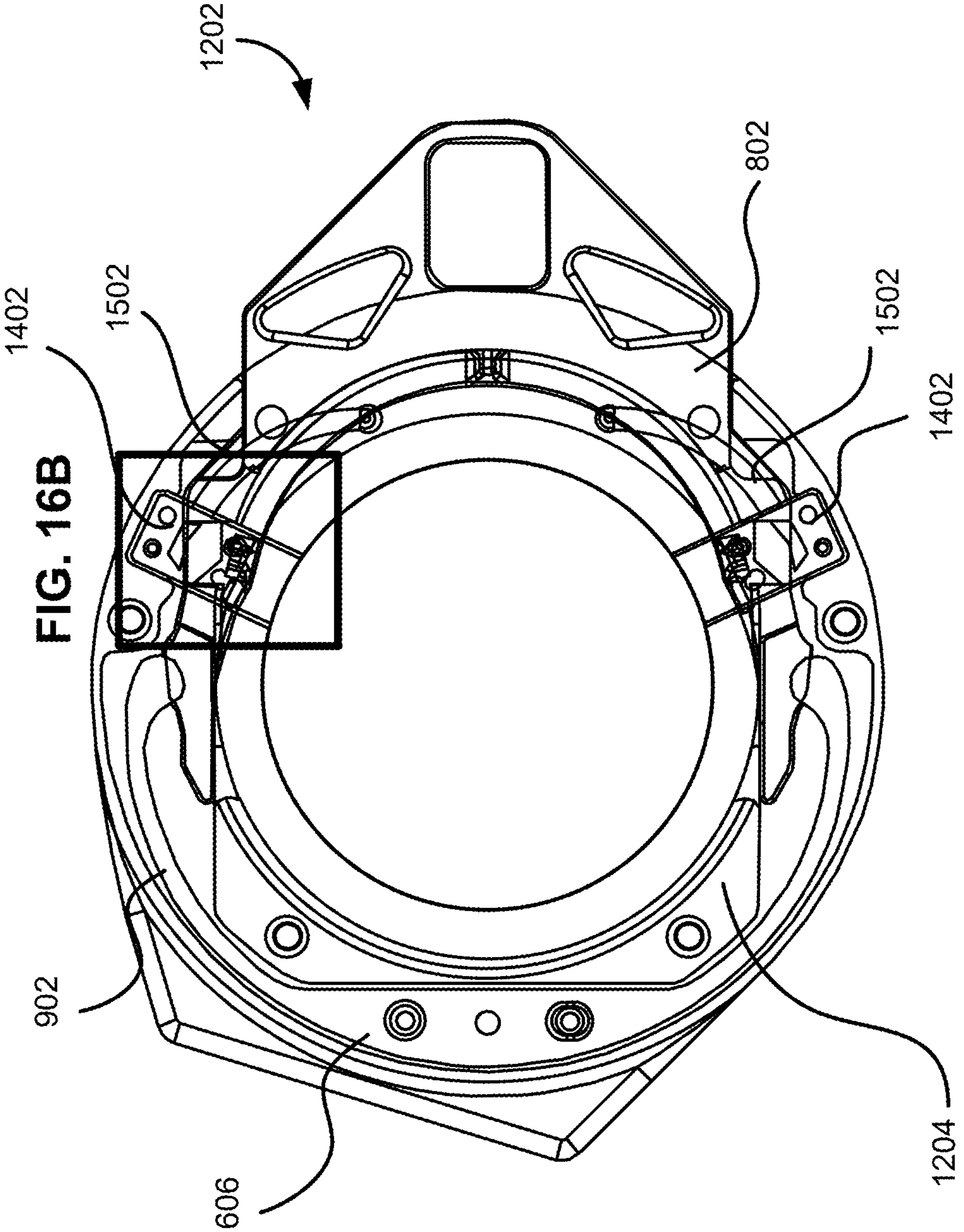
FIG. 16A is a top view of a cuff lock system in a lockout configuration, in accordance with embodiments of the present disclosure.
Figure 16B:
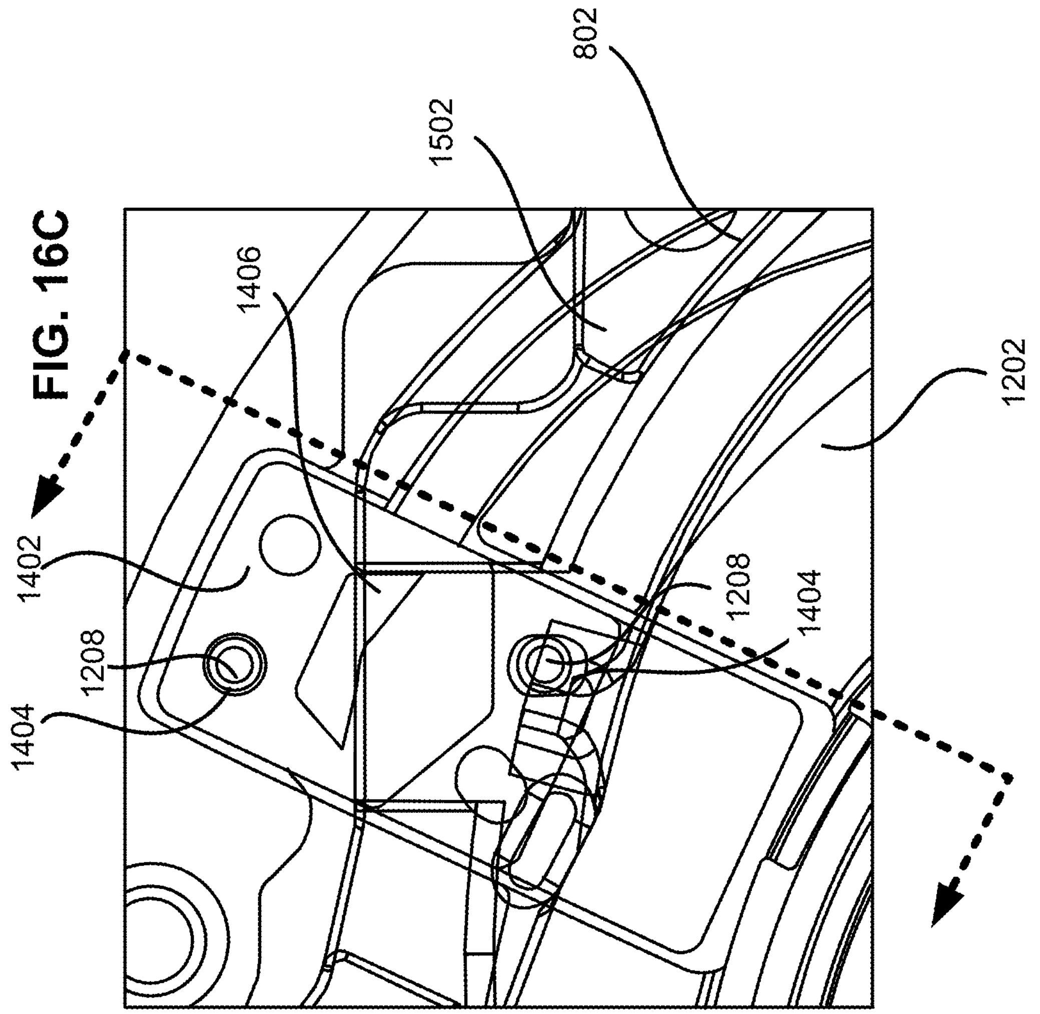
FIG. 16B is an inset of the cuff lock system of FIG. 16A, in accordance with embodiments of the present disclosure.
Figure 16C:
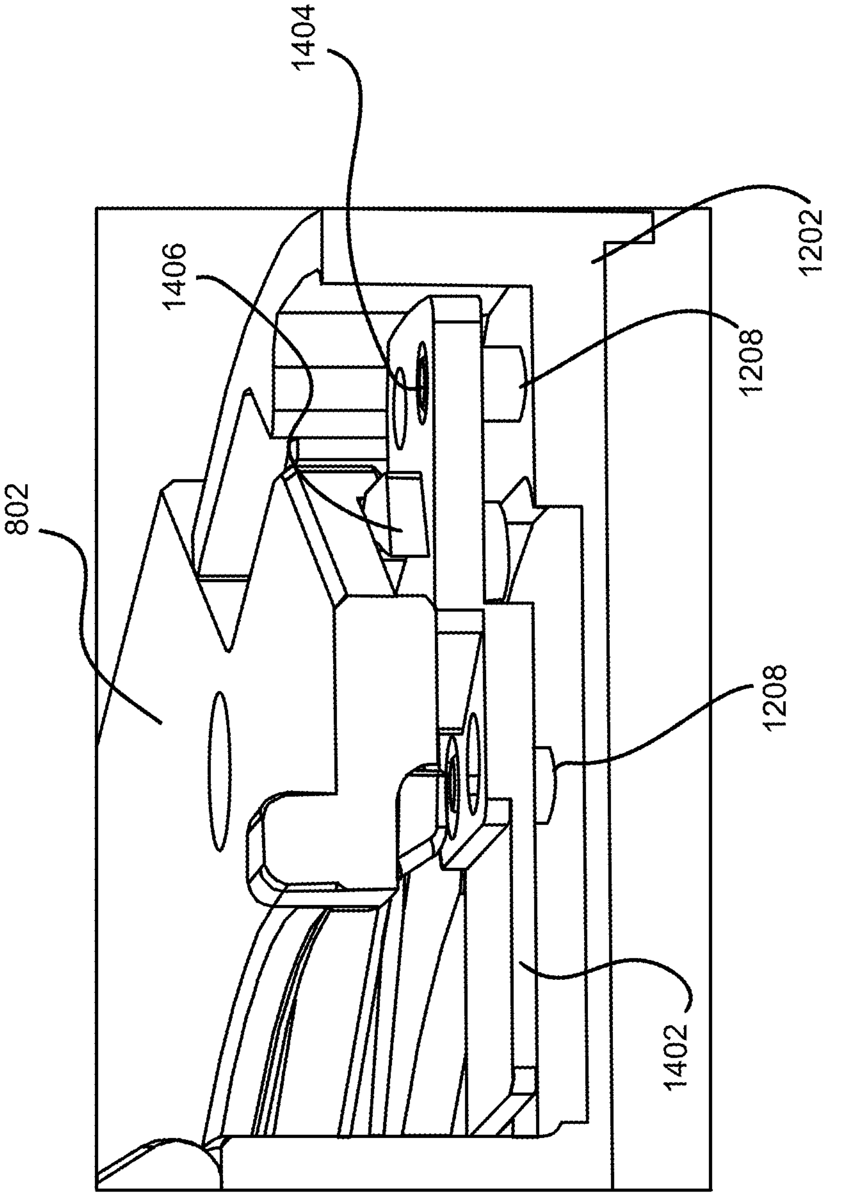
FIG. 16C is a cross-section of the cuff lock system of FIG. 16B, in accordance with embodiments of the present disclosure.
Figure 16D:
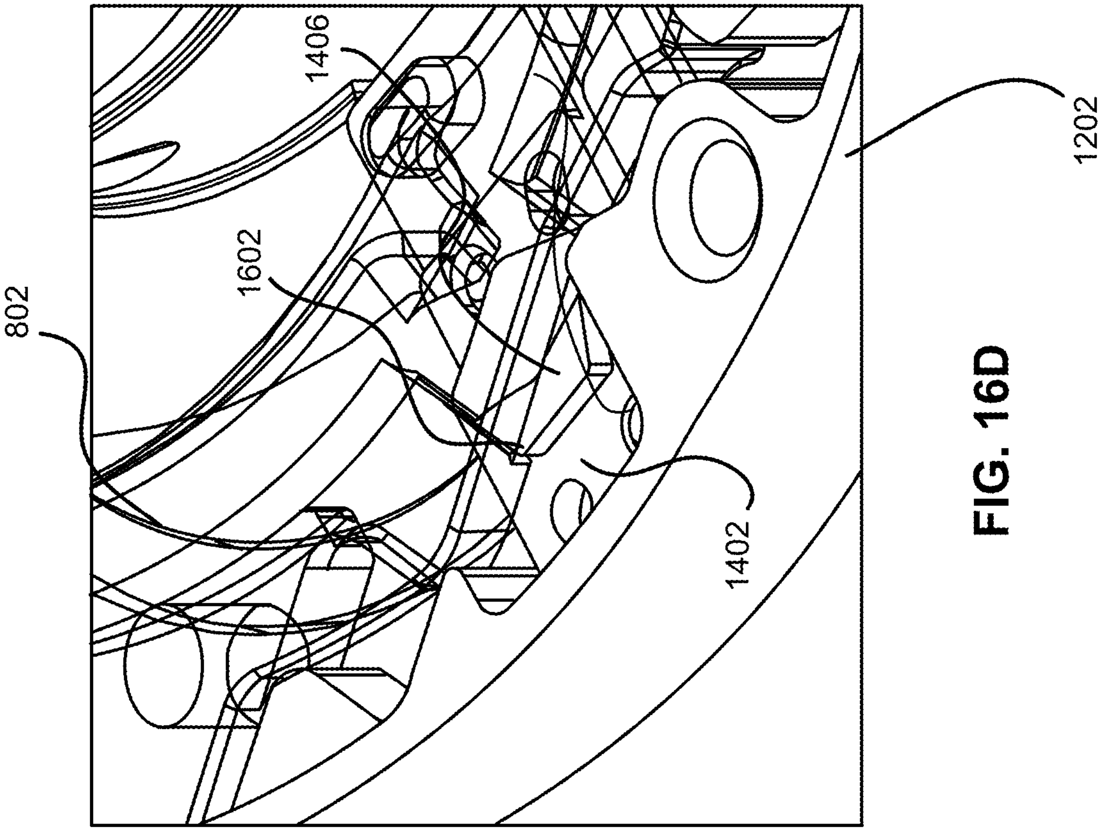
FIG. 16D is a perspective of the cuff lock system of FIG. 16A, in accordance with embodiments of the present disclosure.

FIG. 16A is a top view of a cuff lock system in a lockout configuration. FIG. 16B is an inset of the cuff lock system of FIG. 16A. FIG. 16C is a cross-section of the cuff lock system of FIG. 16B. FIG. 16D is a perspective of the cuff lock system of FIG. 16A. The description of various systems as described with respect to FIGS. 1-15B is relevant to the description of FIGS. 16A-16D. Accordingly, similar components have similar numbering, form, and function unless otherwise noted herein. As shown in FIG. 16A, the springs 1502 contact the underside of the stop component 1402 and push the stop components 1402 up vertically along the posts 1208 machined into the coupling mechanism 1204. This action aligns a stop ledge 1406 with an interfacing ledge of the cuff lock assembly 1202. When the blood pump is not seated into the ventricular cuff, as described in detail above, the stop components 1402 remain elevated by the springs 1502 and the stop ledges 1406 prevent the cuff lock assembly 1202 from advancing to the point where the cuff lock assembly 1202 locks with the spring arm member 606. The elevated stop components 1402 result in a lockout configuration as shown in FIG. 16A. FIG. 16B is an inset illustrating an enlarged view of the cuff lock system of FIG. 16A.

FIG. 16C is a cross-section of the cuff lock system of FIG. 16B showing the stop component 1402 in the elevated position. The vertical wall of the stop ledge 1406 stops forward movement of the cuff lock assembly 1202, resulting in the lockout configuration. FIG. 16D illustrates a top perspective view of the contact point 1602 that prevents the cuff lock assembly 1202 from advancing to the locked position.

Figures 17A, 17B:
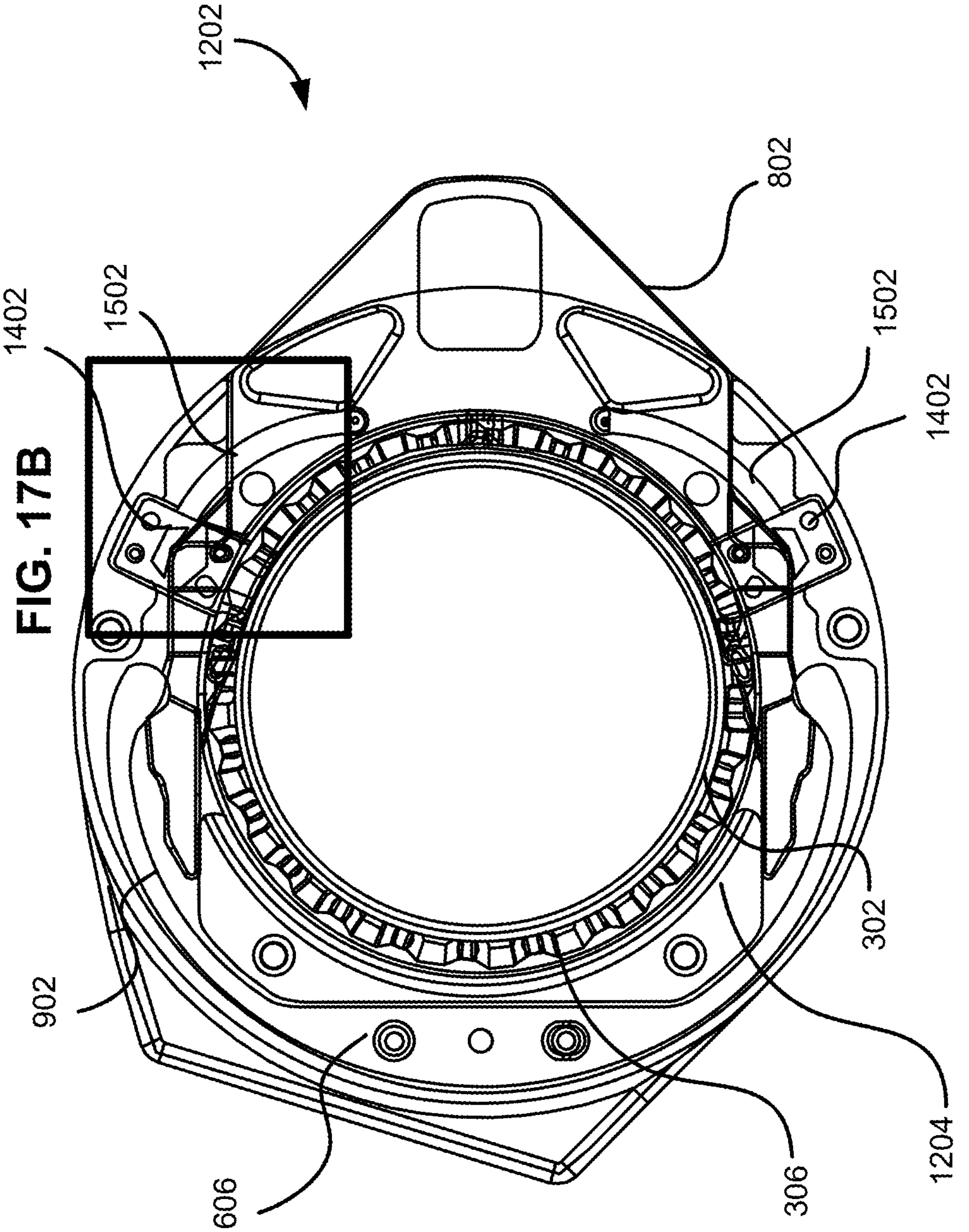
FIG. 17A is a top view of a cuff lock system in a locked configuration, in accordance with embodiments of the present disclosure.
FIG. 17B is an inset of the cuff lock system of FIG. 17A, in accordance with embodiments of the present disclosure.
Figures 17B, 17C:
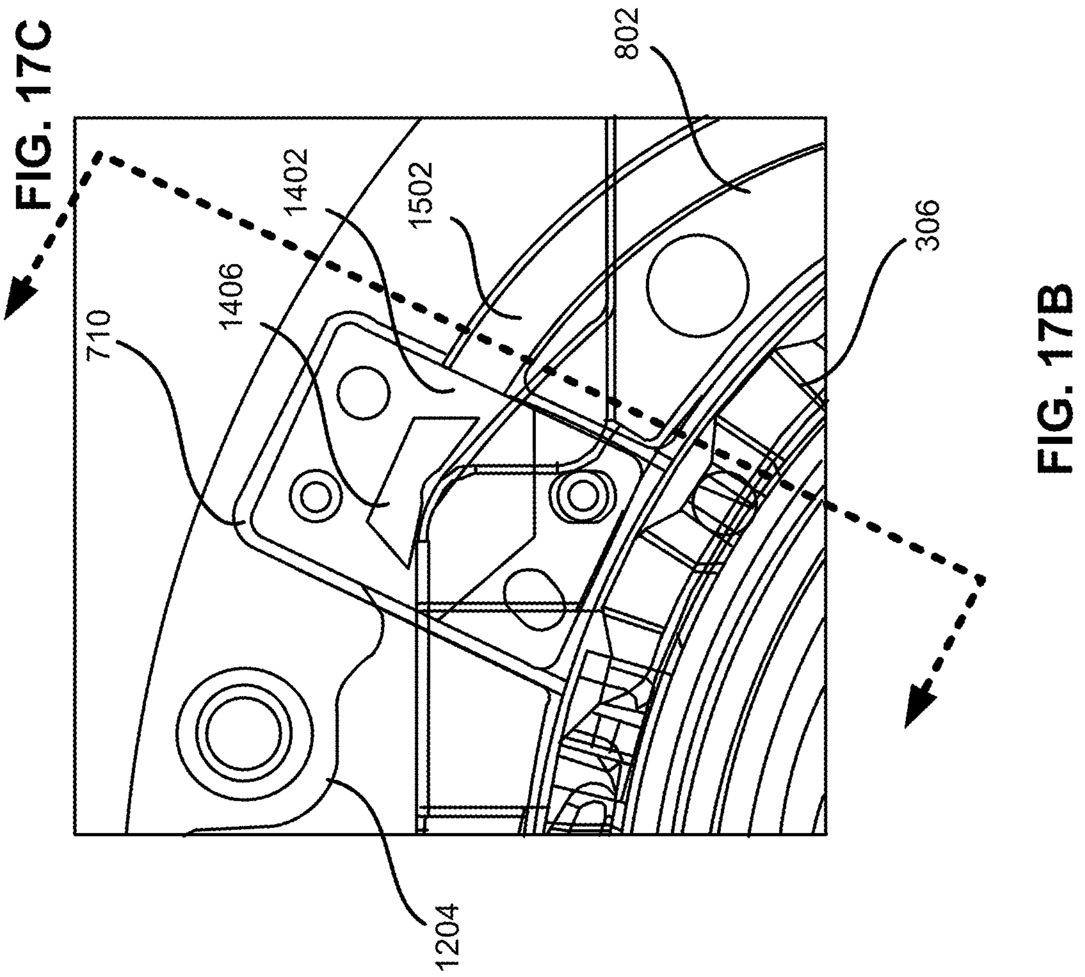
FIG. 17C is a cross-section of the cuff lock system of FIG. 17B, in accordance with embodiments of the present disclosure.
Figure 17C:
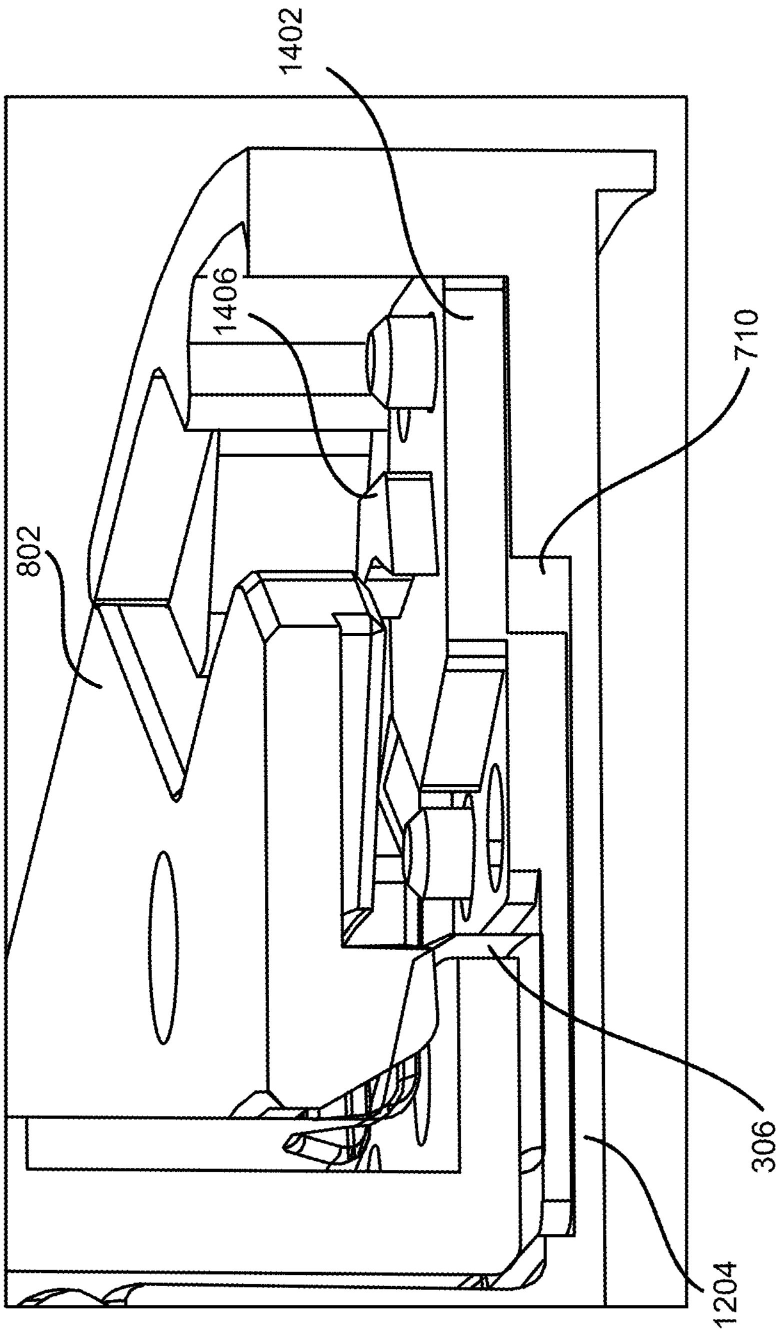
Figure 17D:
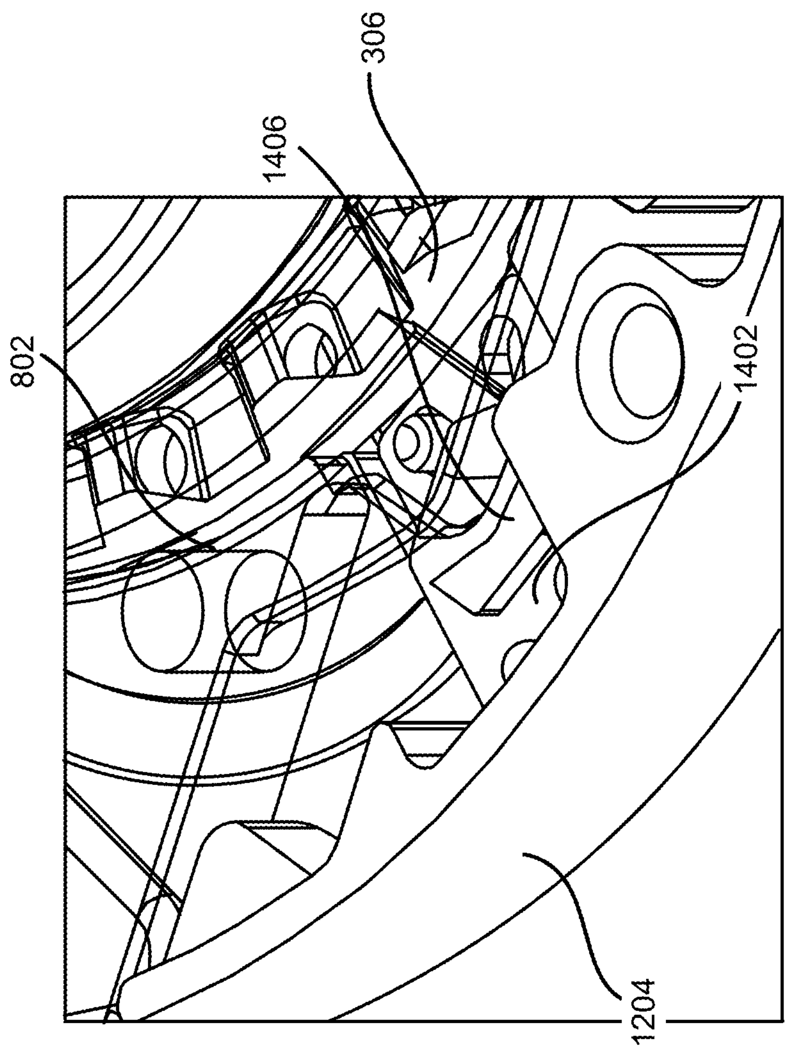
FIG. 17D is a perspective of the cuff lock system of FIG. 17A, in accordance with embodiments of the present disclosure.

FIG. 17A is a top view of a cuff lock system in a locked configuration. FIG. 17B is an inset of the cuff lock system of FIG. 17A. FIG. 17C is a cross-section of the cuff lock system of FIG. 17B. FIG. 17D is a perspective of the cuff lock system of FIG. 17A. The description of various systems as described with respect to FIGS. 1-16D is relevant to the description of FIGS. 17A-17D. Accordingly, similar components have similar numbering, form, and function unless otherwise noted herein. As shown in FIG. 17A, when the ventricular cuff 302 and the flange 306 are properly seated onto the blood pump (e.g., the coupling mechanism 1204 of the blood pump), the flange 306 depresses the stop components 1402 into the recessed detents 710 of the coupling mechanism 1204. This allows for flush seating of the blood pump against the cuff lock assembly 1202, allowing the cuff lock assembly 1202 to travel a longer distance to the point where the spring arm member 606 deflects past the cuff lock arm 802 ridges 806, thereby locking the cuff lock assembly 1202 into place, as described in detail above. FIG. 17B is an inset illustrating an enlarged view of the cuff lock system of FIG. 17A.

FIG. 17C is a cross-section of the cuff lock system of FIG. 17B showing the stop component 1402 in the recessed position in the detents 710 of the coupling mechanism 1204. FIG. 17D illustrates a top perspective view of the stop component 1402 in the recessed position in the detents 710 of the coupling mechanism 1204 that enables the cuff lock arms 802 of the cuff lock assembly 1202 to advance to the locked position.

Figure 18A:
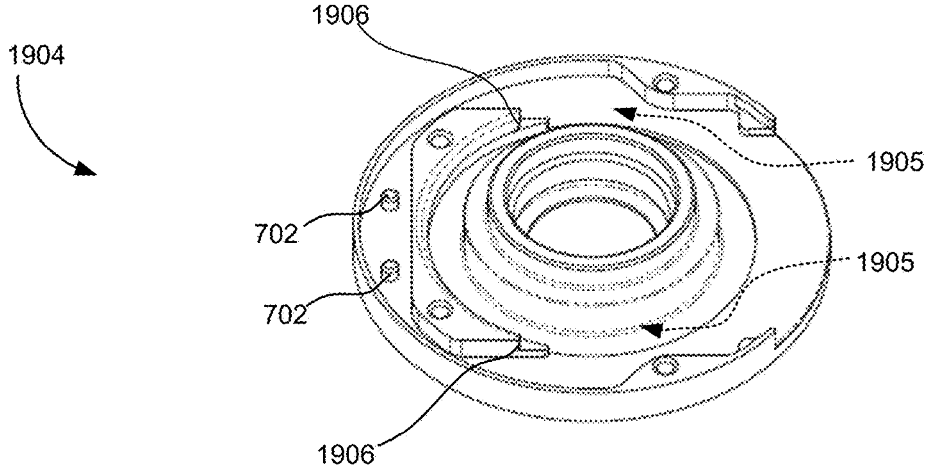
FIG. 18A is a perspective view of a coupling mechanism for a blood pump, in accordance with embodiments of the present disclosure.
Figure 18B:
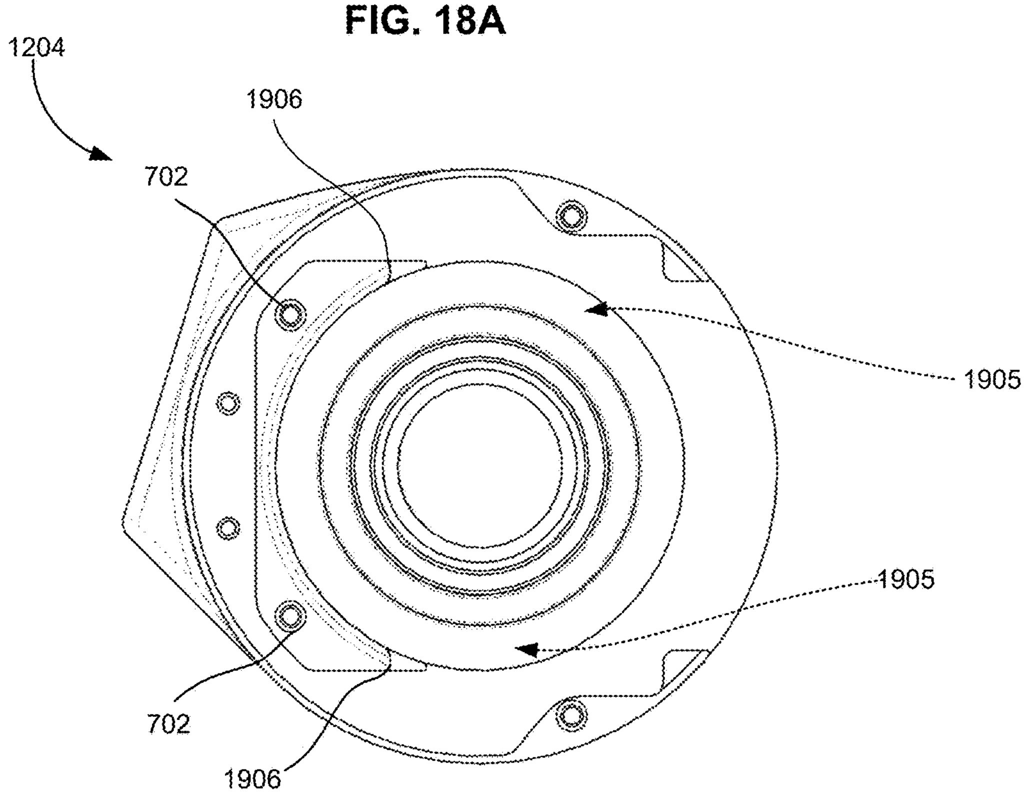
FIG. 18B is a top view of the coupling mechanism of FIG. 18A, in accordance with embodiments of the present disclosure.

FIG. 18A is a perspective view of a coupling mechanism for a blood pump. FIG. 18B is a top view of the coupling mechanism of FIG. 18A. The description of various systems as described with respect to FIGS. 1-17D is relevant to the description of FIGS. 18A-18B. Accordingly, similar components have similar numbering, form, and function unless otherwise noted herein. The coupling mechanism 1904 includes one or more protrusions 702 for securing a spring arm member (such as spring arm member 606) in position. The coupling mechanism 1904 defines cuff lock passages 1905. Cuff lock arms of cuff lock assembly 1902 are slidably disposed within the cuff lock passages 1905 defined by the coupling mechanism 1904. Depending on the positioning of one or more two-part cam components and whether the blood pump is properly seated relative to the ventricular cuff, the cuff lock arms travel along cuff lock passages 1905, to be described in further detail below. The coupling mechanism 1904 further defines one or more stop surfaces 1906 that direct corresponding one or more two-part cam components between a first position and a second position, to be described in further detail below. A first position of the one or more two-part cam components corresponds to the locked position or configuration of the cuff lock assembly. A second position of the one or more two-part cam components corresponds to the lockout position or configuration of the cuff lock assembly.

Figure 19A:
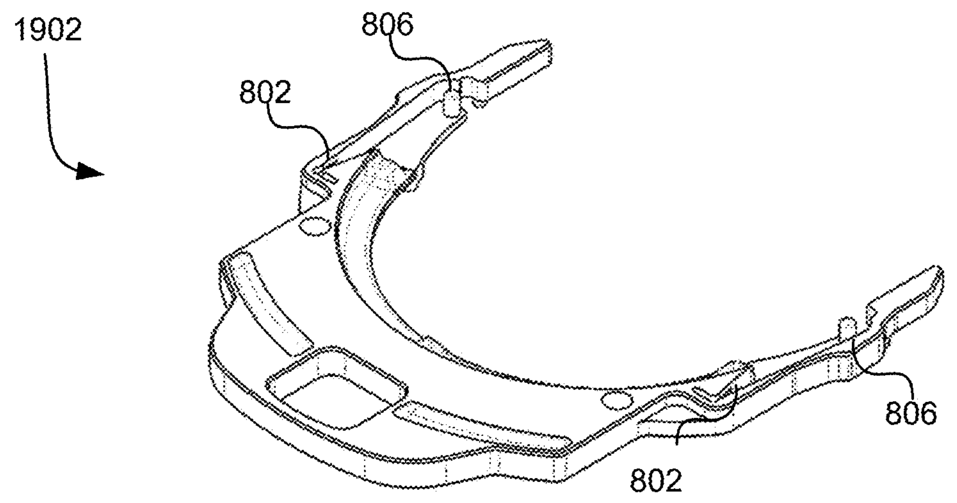
FIG. 19A is a perspective view of a cuff lock assembly, in accordance with embodiments of the present disclosure.
Figure 19B:
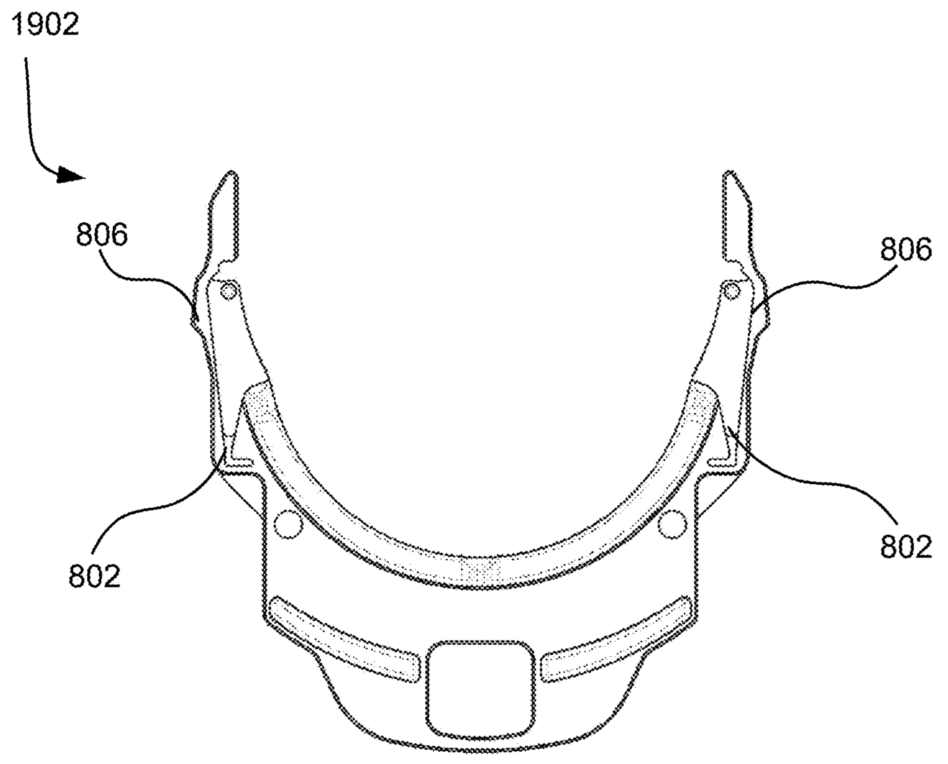
FIG. 19B is a bottom view of the cuff lock assembly of FIG. 19A, in accordance with embodiments of the present disclosure.
Figure 19C:
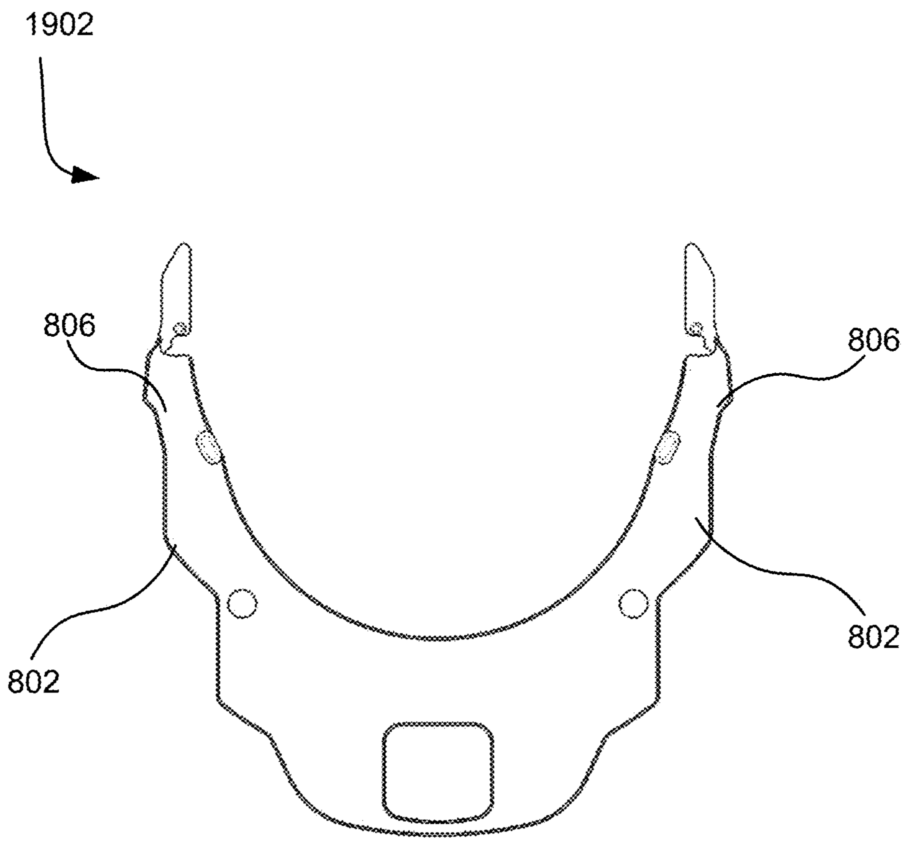
FIG. 19C is a top view of the cuff lock assembly of FIG. 19A, in accordance with embodiments of the present disclosure.

FIG. 19A is a perspective view of a cuff lock assembly. FIG. 19B is a bottom view of the cuff lock assembly of FIG. 19A. FIG. 19C is a top view of the cuff lock assembly of FIG. 19A. The description of various systems as described with respect to FIGS. 1-18B is relevant to the description of FIGS. 19A-19C. Accordingly, similar components have similar numbering, form, and function unless otherwise noted herein. The cuff lock assembly 1902 is repositionable relative to the coupling mechanism between a retracted position and an engaged (e.g., locked) position. For example, the cuff lock assembly 1902 in the retracted position accommodates insertion of the inlet cannula into the inlet cannula passage to mount the blood pump onto the ventricular cuff into a mounted configuration (e.g., a properly seated configuration).

The cuff lock assembly 1902 includes cuff lock arms 802 that are slidably disposed within cuff lock passages 1905 defined by the coupling mechanism 1204 described with respect to FIGS. 18A and 18B. The cuff lock arms 802 are configured to extend over the outward facing circumferential flange 306 of the ventricular cuff 302 as shown at least in FIGS. 3, 4B, and 4C. Furthermore, the cuff lock arms 802 are configured to extend over the outward facing circumferential flange 306 of the ventricular cuff 302 in the mounted configuration when the cuff lock assembly 1902 is in the engaged position to secure the blood pump 204 to the ventricular cuff 302. According to further embodiments, the cuff lock arms 802 include one or more ridges 806 for engaging with and securing the cuff lock arms 802 relative to a spring arm member 606 within the coupling mechanism 1904 similarly to the cuff lock assembly 602 described in detail above.

Figures 20A, 20B:
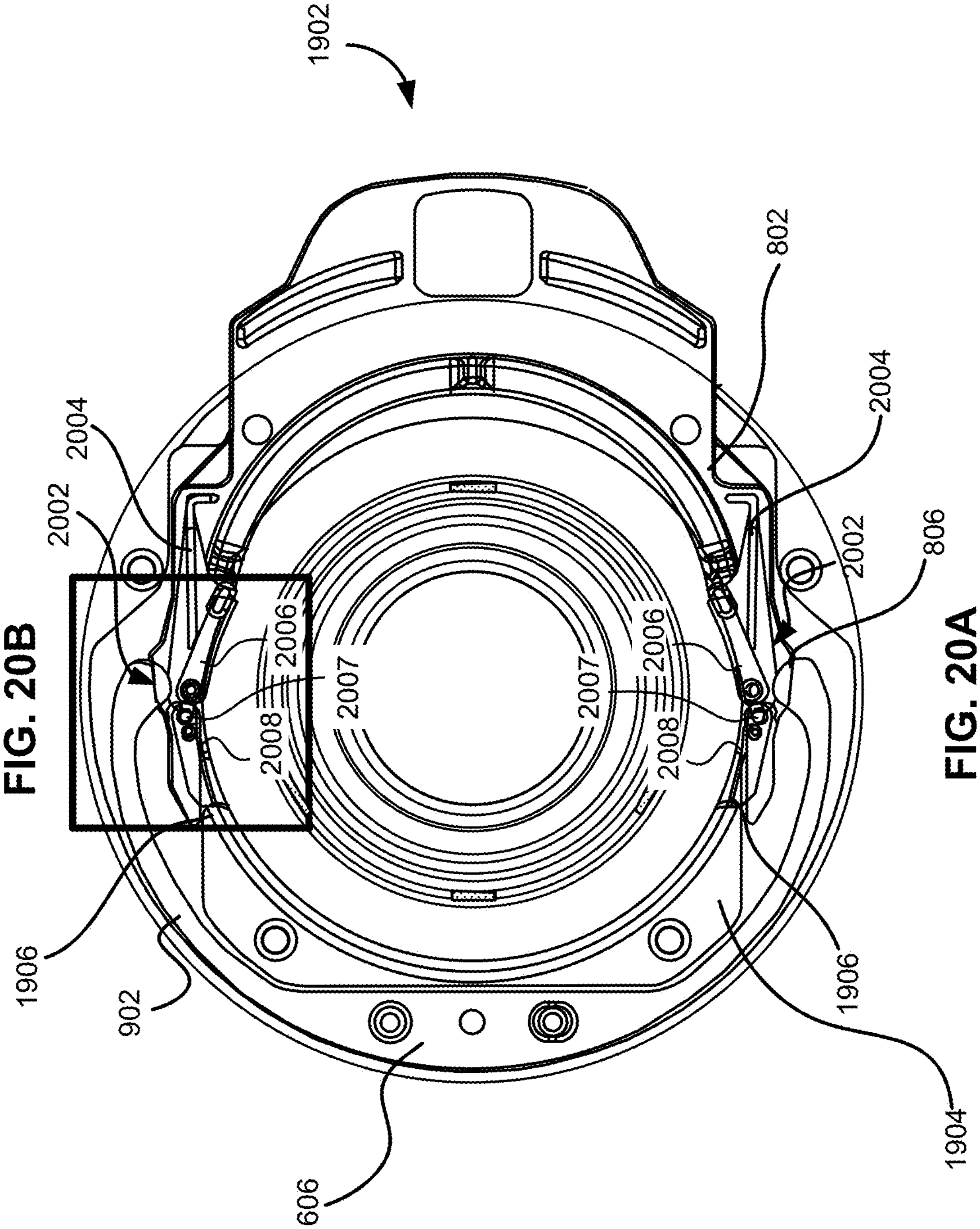
FIG. 20A is a top view of a cuff lock system in a lockout configuration, in accordance with embodiments of the present disclosure.
FIG. 20B is an inset of the cuff lock system of FIG. 20A, in accordance with embodiments of the present disclosure.
Figure 20B:
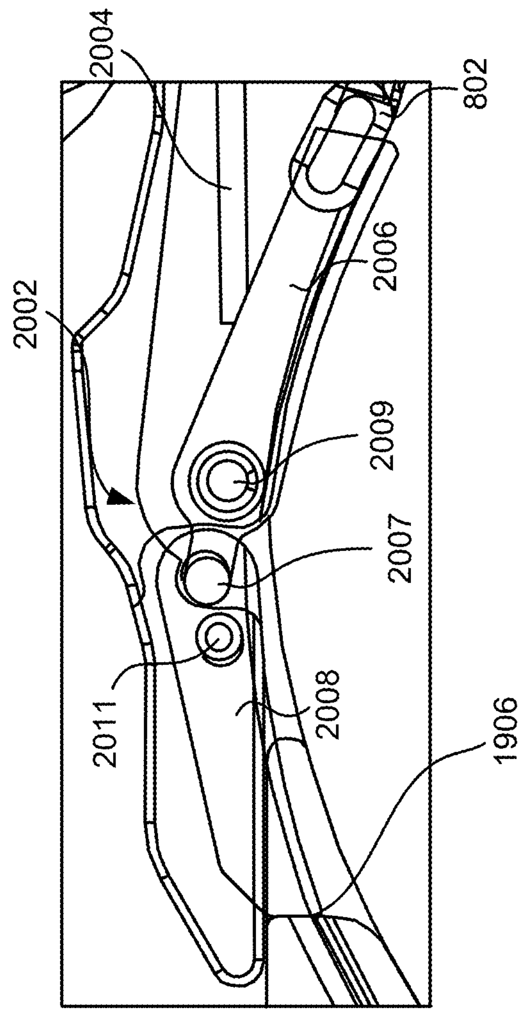
Figure 20C:
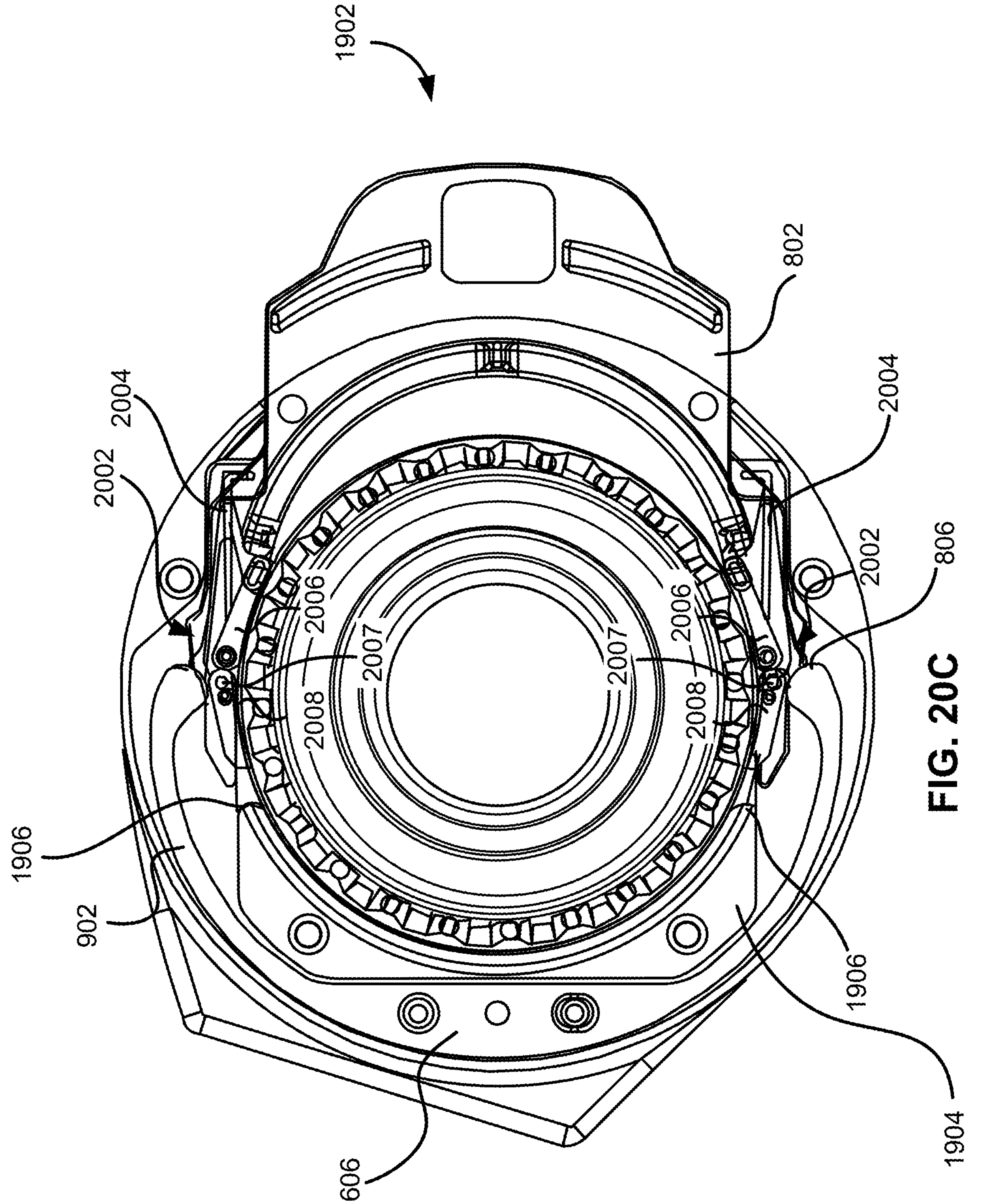
FIG. 20C is a top view of a cuff lock system in a retracted configuration, in accordance with embodiments of the present disclosure.

FIG. 20A is a top view of a cuff lock system in a lockout configuration. FIG. 20B is an inset of the cuff lock system of FIG. 20A. FIG. 20C is a top view of the cuff lock system of FIG. 20C in a retracted configuration. The description of various systems as described with respect to FIGS. 1-19C is relevant to the description of FIGS. 20A-20C. Accordingly, similar components have similar numbering, form, and function unless otherwise noted herein. As shown in FIG. 20A, two-part cam components 2002 are shown in contact with the stop surfaces 1906 of the coupling mechanism 1904 when the blood pump (e.g., the coupling mechanism 1904 of the blood pump) is not seated relative to the ventricular cuff. Springs 2004 contact a first part 2006 of the two-part cam component 2002 and keep the two-part cam component 2002 captive by a corresponding moveable post 2007 in the cuff lock assembly 1902. The angle of the second part 2008 of the two-part cam component 2002 is controlled by the position (e.g., the angle) of the first part 2006. The spring 2004 biases the first part 2006 inward toward the center of the coupling mechanism 1904, thereby pushing the moveable post 2007 up and away from the center of the coupling mechanism 1904. When the blood pump is not seated, as shown in FIG. 20A, the cuff lock assembly 1902 and the two-part cam component 2002 travel together in this orientation and eventually, the stop surface 1906 abuts the second part 2008 of the two-part cam component 2002 as shown in FIG. 20A and further detailed in the enlarged view shown in FIG. 20B. The interaction between the two-part cam component 2002 and the stop surface 1906 creates the lockout configuration where the cuff lock assembly 1902 is prevented from advancing to the locked configuration.

Figure 21A:
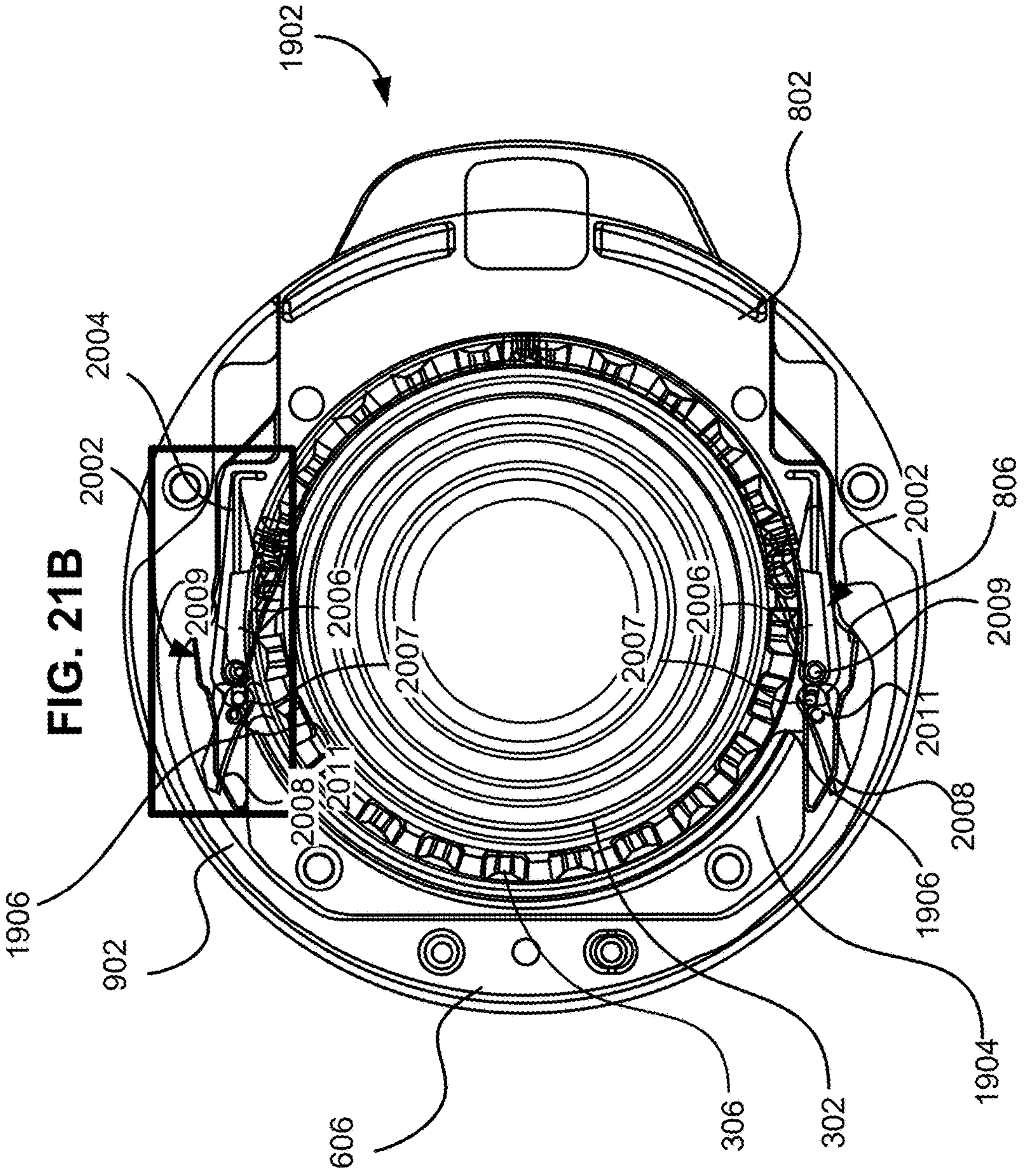
FIG. 21A is a top view of a cuff lock system in a locked configuration, in accordance with embodiments of the present disclosure.
Figure 21B:
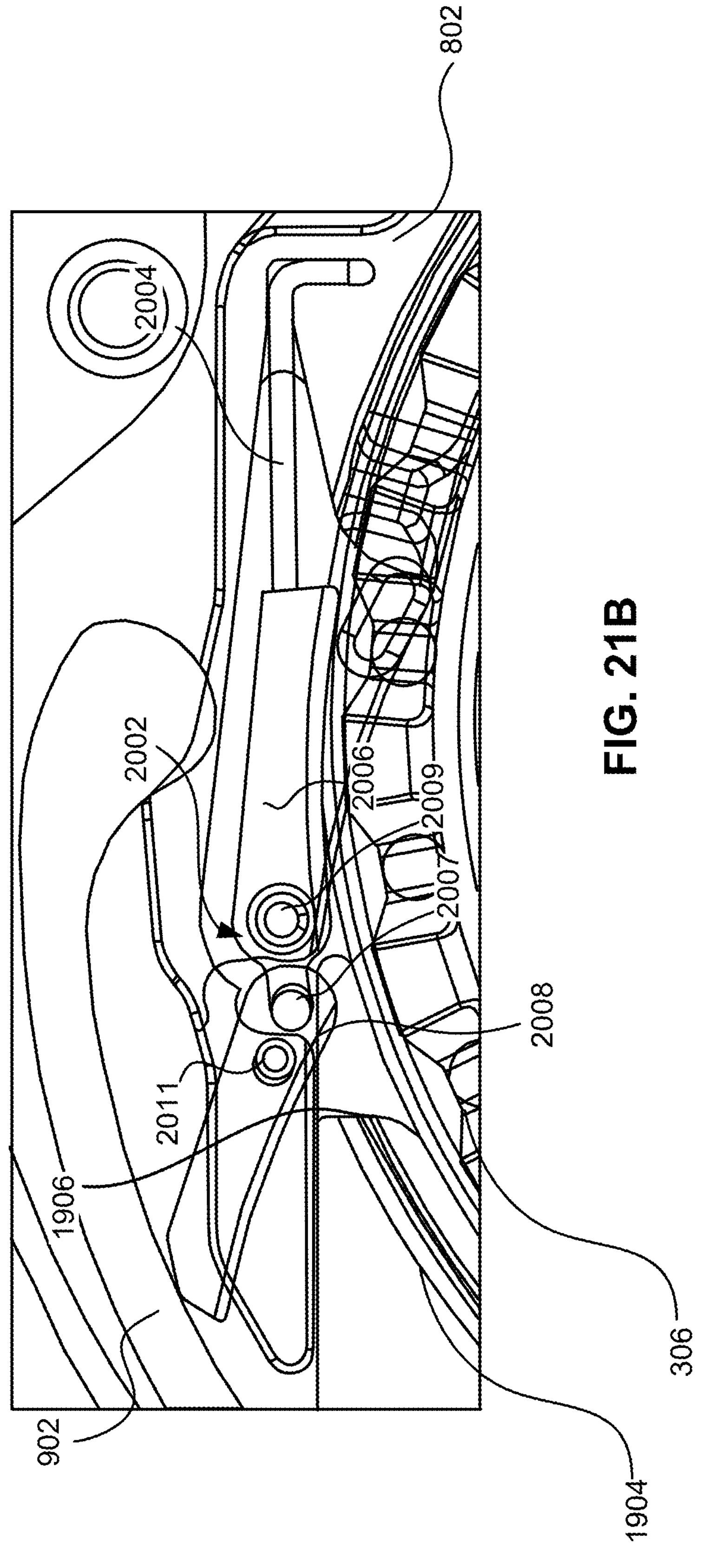
FIG. 21B is an inset of the cuff lock system of FIG. 21A, in accordance with embodiments of the present disclosure.

FIG. 21A is a top view of a cuff lock system in a locked configuration. FIG. 21B is an inset of the cuff lock system of FIG. 21A. The description of various systems as described with respect to FIGS. 1-20C is relevant to the description of FIGS. 21A-21B. Accordingly, similar components have similar numbering, form, and function unless otherwise noted herein. As shown in FIG. 21A, when the blood pump (e.g., the coupling mechanism 1904 of the blood pump) is properly seated onto the ventricular cuff 302 and the flange 306, the flange 306 interacts with the two-part cam component 2002 and the spring 2004 is pushed from the extended position to the flexed position. As the cuff lock assembly 1902 advances, the flange 306 pushes the first part 2006 of the two-part cam component 2002 against the spring 2004, causing the spring 2004 to flex away from the center of the coupling mechanism 1904. According to various embodiments, the springs 2004 may be made of various materials and dimensions for fine tuning the force applied to the first part 2006, in a manner that would be appreciated by one having ordinary skill in the art upon reading the present disclosure. In further embodiments, the springs 2004 may include geometries other than those shown in FIGS. 21A-21B. The flange 306 also causes the first part 2006 to rotate about a first fixed post 2009 in the cuff lock assembly 1902. The moveable post 2007 is directed towards the center of the coupling mechanism 1904, which causes the second part 2008 to rotate about a second fixed post 2011 so that the free end is directed lateral to the stop surface 1906 of the coupling mechanism 1904, bypassing it as the cuff lock assembly 1902 advances. The cuff lock assembly 1902 is able to advance to the locked position having the flexible arms 902 of the spring arm member 606 engage and secure the ridges 806 of the cuff lock arms 802, as described in detail above. FIG. 21B is an inset illustrating an enlarged view of the cuff lock system of FIG. 21A.

Figure 22:
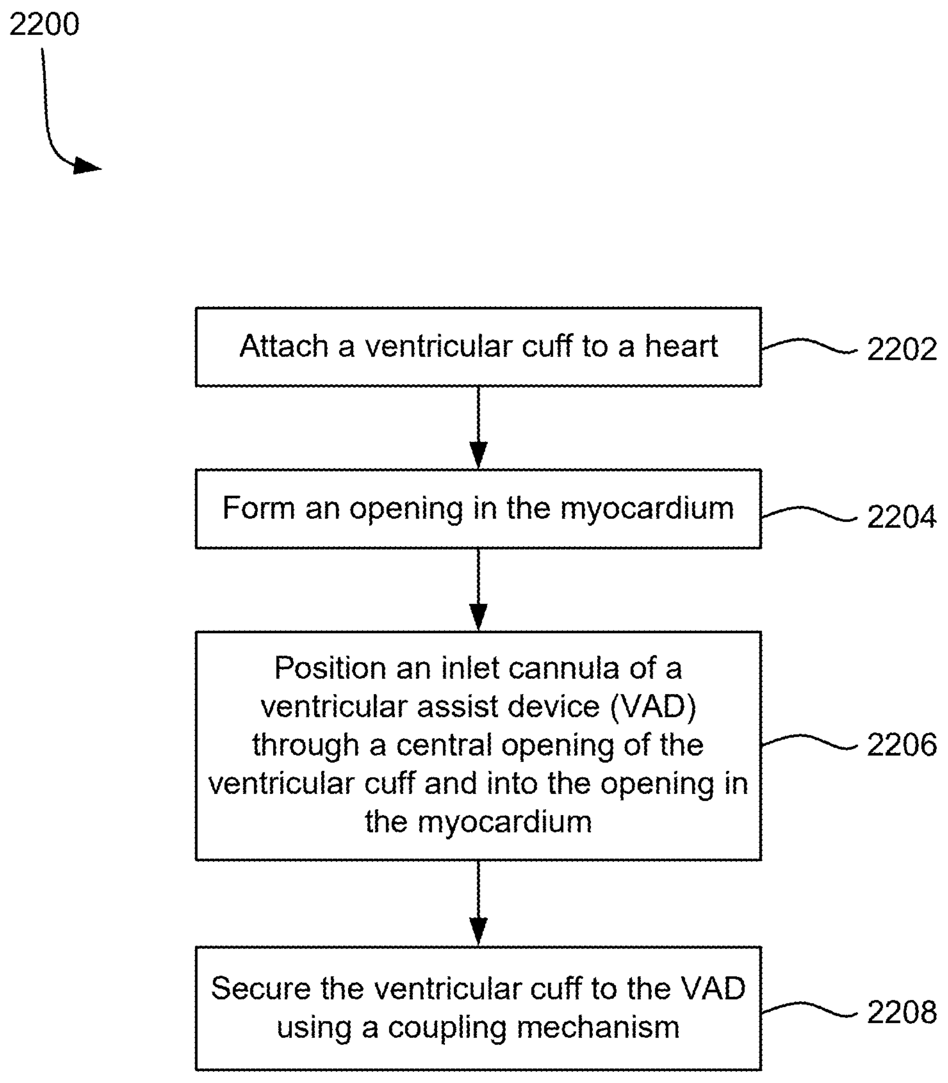
FIG. 22 is a flowchart of a method, in accordance with embodiments of the present disclosure.

FIG. 22 is a flowchart of a method of securing a ventricular assist device (VAD) to a ventricular cuff attached to a heart. Method 2200 includes step 2202 attaching a ventricular cuff to a heart. The ventricular cuff includes an outward facing circumferential flange having a groove. Step 2204 includes forming an opening in the myocardium. According to various embodiments, step 2204 and step 2202 may be performed interchangeably, depending on surgeon preference. For example, the surgeon may form the opening in the myocardium prior to attaching the ventricular cuff to the heart. Step 2206 includes positioning an inlet cannula of a ventricular assist device (VAD) through a central opening of the ventricular cuff and into the opening in the myocardium. Step 2208 includes securing the ventricular cuff to the VAD using a coupling mechanism. A coupling mechanism may be used with a cuff lock assembly. Any combination of embodiments described in detail above to provide a cuff lock assembly that securely couples to the coupling mechanism thereby securing the ventricular cuff to the VAD.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A ventricular assist device (VAD) comprising:
- an inlet cannula;
- a blood flow outlet;
- a blood pump assembly operable to pump blood from the inlet cannula to the blood flow outlet; and
- a coupling mechanism operable to secure the blood pump to a ventricular cuff attached to a heart, wherein:
- the ventricular cuff defines an inlet cannula passage for the inlet cannula and an outward facing circumferential flange having a groove;
- the coupling mechanism comprises a coupling mechanism housing, a spring arm member attached to the coupling mechanism housing, and a cuff lock assembly comprising cuff lock arms slidably disposed within cuff lock passages defined by the coupling mechanism housing;
- the cuff lock assembly is repositionable relative to the coupling mechanism housing between an unlocked position and a locked position;
- the cuff lock assembly in the unlocked position accommodates insertion of the inlet cannula into the inlet cannula passage to mount the blood pump onto the ventricular cuff into a mounted configuration;
- the cuff lock arms are configured to extend onto the outward facing circumferential flange of the ventricular cuff in the mounted configuration when the cuff lock assembly is in the locked position to secure the blood pump to the ventricular cuff;
- the spring arm member comprises flexible arms configured to engage the cuff lock arms in the locked position to inhibit repositioning of the cuff lock arms relative to the coupling mechanism housing; and
- the coupling mechanism is configured to accommodate repositioning of the cuff lock assembly from the unlocked position to the locked position when the blood pump is in the mounted configuration and block repositioning of the cuff lock assembly from the unlocked position to the locked position when the blood pump is not in the mounted configuration.

2. The ventricular assist device (VAD) of claim 1, wherein, when the VAD is properly seated relative to the ventricular cuff, the cuff lock assembly is positionable in the locked position, and, when the VAD is not properly seated relative to the ventricular cuff, the cuff lock assembly is prevented from reaching the locked position.

3. The ventricular assist device (VAD) of claim 1, wherein the coupling mechanism further comprises two pivoting components to enable the cuff lock assembly to be positioned in the locked position or prevent the cuff lock assembly from reaching the locked position.

4. The ventricular assist device (VAD) of claim 3, wherein, when the VAD is properly seated relative to the ventricular cuff, the flange directs the two pivoting components to a first position that enables the cuff lock assembly to reach the locked position.

5. The ventricular assist device (VAD) of claim 3, wherein, when the VAD is not properly seated relative to the flange of the ventricular cuff, the two pivoting components are in a second position that prevents the cuff lock assembly from reaching the locked position.

6. The ventricular assist device (VAD) of claim 3, wherein the cuff lock passages define detents for protrusions of each of the two pivoting components to travel along.

7. The ventricular assist device (VAD) of claim 1, wherein each flexible arm of the spring arm member engages with corresponding ridges on cuff lock arms when the cuff lock assembly is in the locked position.

8. The ventricular assist device (VAD) of claim 1, wherein:
- the inlet cannula has a longitudinal axis; and
- the cuff lock assembly moves, relative to the cuff, from the unlocked position to the locked position transverse to the longitudinal axis.

9. The ventricular assist device (VAD) of claim 8, wherein the cuff lock assembly moves, relative to the cuff, from the unlocked position to the locked position in a plane perpendicular to the longitudinal axis.

10. The ventricular assist device (VAD) of claim 1, wherein the cuff lock assembly further includes a visual indicator, wherein the visual indicator is exposed when the cuff lock assembly is not in the locked position, and wherein the visual indicator is obscured when the cuff lock assembly is in the locked position.

11. The ventricular assist device (VAD) of claim 1, further comprising one or more stop components for engaging the cuff lock assembly and impeding the cuff lock assembly from reaching the locked position or enabling the cuff lock assembly to reach the locked position.

12. The ventricular assist device (VAD) of claim 11, wherein, when the flange of the cuff is properly seated, the flange compresses the one or more stop components to a first position that enables the cuff lock assembly to reach the locked position.

13. The ventricular assist device (VAD) of claim 11, wherein, when the flange of the cuff is not properly seated, the one or more stop components is raised to a second position by a spring, the second position preventing the cuff lock assembly from reaching the locked position.

14. The ventricular assist device (VAD) of claim 11, wherein the cuff lock passages define detents for protrusions of each of the one or more stop components to settle in.

15. The ventricular assist device (VAD) of claim 11, wherein the one or more stop components comprise a two-part cam component mechanism.

16. A method of securing a ventricular assist device (VAD) to a ventricular cuff attached to a heart, the method comprising:
- attaching a ventricular cuff to a heart, the ventricular cuff comprising an outward facing circumferential flange having a groove;
- forming an opening in the myocardium;
- positioning an inlet cannula of a ventricular assist device (VAD) through a central opening of the ventricular cuff and into the opening in the myocardium; and
- securing the ventricular cuff to the VAD using a coupling mechanism, wherein:

the coupling mechanism comprises a coupling mechanism housing, a spring arm member attached to the coupling mechanism housing, and a cuff lock assembly comprising cuff lock arms slidably disposed within cuff lock passages defined by the coupling mechanism housing;

the cuff lock assembly is repositionable relative to the coupling mechanism housing between an unlocked position and a locked position;

the cuff lock assembly in the unlocked position accommodates insertion of the inlet cannula into the inlet cannula passage to mount the VAD onto the ventricular cuff into a mounted configuration;

the cuff lock arms are configured to extend over the outward facing circumferential flange of the ventricular cuff in the mounted configuration when the cuff lock assembly is in the locked position to secure the VAD to the ventricular cuff;

the spring arm member comprises flexible arms configured to engage the cuff lock arms in the locked position to inhibit repositioning of the cuff lock arms relative to the coupling mechanism housing; and the coupling mechanism is configured to accommodate repositioning of the cuff lock assembly from the unlocked position to the locked position in the mounted configuration and block repositioning of the cuff lock assembly from the unlocked position to the locked position when the VAD is not in the mounted configuration.

17. The method of claim 16, wherein each flexible arm of the spring arm member engages with corresponding ridges on cuff lock arms when the cuff lock assembly is in the locked position.

18. The method of claim 16, wherein the coupling mechanism further comprises two pivoting components to enable the cuff lock assembly to be positioned in the locked position or prevent the cuff lock assembly from reaching the locked position.

19. The method of claim 16, wherein the cuff lock assembly further includes a visual indicator, wherein the visual indicator is exposed when the cuff lock assembly is not in the locked position, and wherein the visual indicator is obscured when the cuff lock assembly is in the locked position.

20. The method of claim 16, wherein:

the inlet cannula has a longitudinal axis; and the cuff lock assembly moves, relative to the cuff, from the unlocked position to the locked position transverse to the longitudinal axis.

* * * * *